US010105417B2

(12) United States Patent
McSweeney et al.

(10) Patent No.: US 10,105,417 B2
(45) Date of Patent: Oct. 23, 2018

(54) METHODS AND KITS FOR MAINTAINING PREGNANCY, TREATING FOLLICULAR CYSTS, AND SYNCHRONIZING OVULATION USING LUTEINIZING HORMONE

(75) Inventors: Kevin McSweeney, Loveland, CO (US); Mark Colgin, Castle Rock, CO (US); Diane Newman, Littleton, CO (US); Jay W. Roth, Golden, CO (US); Roger Hurst, Castle Rock, CO (US)

(73) Assignee: AspenBio Pharma, Inc., Castle Rock, CO (US)

( * ) Notice: Subject to any disclaimer, the term of this patent is extended or adjusted under 35 U.S.C. 154(b) by 1163 days.

(21) Appl. No.: 10/795,128

(22) Filed: Mar. 4, 2004

(65) Prior Publication Data

US 2004/0266697 A1 Dec. 30, 2004

Related U.S. Application Data

(60) Provisional application No. 60/452,297, filed on Mar. 4, 2003, provisional application No. 60/516,002, filed on Oct. 31, 2003.

(51) Int. Cl.
*A61K 38/24* (2006.01)
*A61D 19/00* (2006.01)

(52) U.S. Cl.
CPC .............. *A61K 38/24* (2013.01); *A61D 19/00* (2013.01)

(58) Field of Classification Search
None
See application file for complete search history.

(56) References Cited

U.S. PATENT DOCUMENTS

| | | | |
|---|---|---|---|
| 2,799,621 A | 7/1957 | Steelman et al. | |
| 3,574,829 A * | 4/1971 | Wagner et al. | 514/12 |
| 3,636,193 A * | 1/1972 | Wagner et al. | 424/546 |
| 3,674,865 A * | 7/1972 | Donini | 530/398 |
| 3,832,469 A | 8/1974 | Downey et al. | |
| 3,892,855 A | 7/1975 | Short | |
| 3,947,569 A | 3/1976 | Immer et al. | |
| 4,089,951 A | 5/1978 | Furr | |
| 4,399,216 A | 8/1983 | Axel et al. | |
| 4,599,227 A | 7/1986 | Dees et al. | |
| 4,610,687 A | 9/1986 | Fogwell | |
| 4,634,665 A | 1/1987 | Axel et al. | |
| 4,673,665 A | 6/1987 | Humke | |
| 4,686,103 A | 8/1987 | Anderson | |
| 4,780,451 A | 10/1988 | Donaldson | |
| 4,840,896 A | 6/1989 | Reddy et al. | |
| 4,873,316 A | 10/1989 | Meade et al. | |
| 4,923,805 A | 5/1990 | Reddy et al. | |
| 4,997,646 A | 3/1991 | Hansen et al. | |
| 4,997,816 A | 3/1991 | Hyland et al. | |
| 5,008,244 A | 4/1991 | Miller et al. | |
| 5,156,957 A | 10/1992 | Reddy et al. | |
| 5,162,306 A | 11/1992 | Donaldson | |
| 5,177,193 A | 1/1993 | Boime et al. | |
| 5,179,017 A | 1/1993 | Axel et al. | |
| 5,240,832 A | 8/1993 | Kelton et al. | |
| 5,240,922 A | 8/1993 | O'Neill | |
| 5,322,775 A | 6/1994 | Clark et al. | |
| 5,338,835 A | 8/1994 | Boime | |
| 5,366,888 A | 11/1994 | Fry et al. | |
| 5,405,945 A | 4/1995 | Boime et al. | |
| 5,508,261 A | 4/1996 | Moyle et al. | |
| 5,585,345 A | 12/1996 | Boime | |
| 5,589,457 A * | 12/1996 | Wiltbank et al. | 514/12 |
| 5,602,006 A | 2/1997 | Kelton et al. | |
| 5,610,138 A | 3/1997 | Jacobs | |
| 5,639,639 A | 6/1997 | Reddy et al. | |

(Continued)

FOREIGN PATENT DOCUMENTS

| | | |
|---|---|---|
| EP | 0310288 | 4/1989 |
| GB | 1 161 836 | 8/1969 |

(Continued)

OTHER PUBLICATIONS

Binelli M. et al, Antiluteolytic Strategies to Improve Fertility in Cattle, Theriogenology (2001), vol. 56, 1451-1483 (from Applicant's IDS).*
Mukku VR et al, "In vitro responsiveness of hamster corpora lutea undergoing luteolysis to luteinizing hormone," J. Biosci., vol. 1, No. 4, Dec. 1979, pp. 457-465.*
Henricks DM, Dickey JF, Niswender GD. "Serum luteinizing hormone and plasma progesterone levels during the estrous cycle and early pregnancy in cows," Biol Reprod. Jun. 1970;2(3):346-51.*

(Continued)

*Primary Examiner* — Thomas S Heard
(74) *Attorney, Agent, or Firm* — Leydig, Voit & Mayer, Ltd.

(57) ABSTRACT

This invention provides methods and kits for maintaining pregnancy in mammals. Pregnancy is maintained by administration of effective amounts of luteinizing hormone (LH) or chorionic gonadotropin (CG). Both LH and CG may be used alone, in combination with each other, or in combination with growth hormone (GH) or follicle stimulating hormone (FSH). Hormones are administered on about Day 4 to about Day 7 following insemination. Effective amounts of LH range from about 10 micrograms to about 25 milligrams, preferably about 2 to about 8 mg, and of CG range from about 100 IU (international units) to about 2000 IU. Mammals treatable by the methods of this invention include ungulates and related mammals, including bovines. Kits provided by this invention include effective amounts of one or more hormones, a device for administering the hormone(s) and instructions. This invention also provides methods for treating follicular cysts and for synchronizing ovulation in mammals using LH.

12 Claims, 2 Drawing Sheets
Specification includes a Sequence Listing.

(56) References Cited

U.S. PATENT DOCUMENTS

| | | |
|---|---|---|
| 5,639,640 A | 6/1997 | Reddy et al. |
| 5,658,760 A | 8/1997 | Kelton et al. |
| 5,674,711 A | 10/1997 | Kelton et al. |
| 5,705,478 A | 1/1998 | Boime |
| 5,712,122 A | 1/1998 | Boime et al. |
| 5,733,735 A | 3/1998 | Boime et al. |
| 5,759,818 A | 6/1998 | Boime |
| 5,767,251 A | 6/1998 | Reddy et al. |
| 5,792,460 A | 8/1998 | Sharp et al. |
| 5,792,785 A | 8/1998 | Sharp et al. |
| 5,856,137 A | 1/1999 | Reddy et al. |
| 5,883,073 A | 3/1999 | Boime et al. |
| 5,929,028 A | 7/1999 | Skrabanja et al. |
| 5,958,737 A | 9/1999 | Boime et al. |
| 5,968,513 A * | 10/1999 | Gallo et al. ............... 424/185.1 |
| 5,985,611 A | 11/1999 | Boime et al. |
| 5,990,288 A | 11/1999 | Musick et al. |
| 6,028,177 A | 2/2000 | Boime et al. |
| 6,087,352 A | 7/2000 | Trout |
| 6,103,501 A | 8/2000 | Boime et al. |
| 6,111,165 A | 8/2000 | Berg |
| 6,183,987 B1 * | 2/2001 | van de Wiel et al. ....... 435/69.1 |
| 6,225,449 B1 | 5/2001 | Boime |
| 6,238,890 B1 | 5/2001 | Boime et al. |
| 6,242,580 B1 * | 6/2001 | Boime et al. ............... 530/398 |
| 6,403,631 B1 | 6/2002 | Sharp et al. |
| 6,414,123 B1 | 7/2002 | Musick et al. |
| 6,455,275 B1 | 9/2002 | Axel et al. |
| 6,455,282 B1 | 9/2002 | Beck et al. |
| 6,472,584 B1 | 10/2002 | Smith |
| 6,528,699 B1 | 3/2003 | Meade et al. |
| 6,635,256 B1 | 10/2003 | Boime et al. |
| 6,635,739 B2 | 10/2003 | Siler-Khodr |
| 6,737,515 B2 | 5/2004 | Boime et al. |
| 7,053,054 B2 | 5/2006 | Paradisi et al. |
| 2001/0041697 A1 | 11/2001 | Foster et al. |
| 2002/0160944 A1 | 10/2002 | Boime et al. |
| 2003/0018037 A1 | 1/2003 | Westbrook et al. |
| 2003/0059898 A1 | 3/2003 | Beck et al. |
| 2004/0006018 A1 | 1/2004 | Baker et al. |
| 2004/0204358 A1 | 10/2004 | Brown et al. |
| 2006/0052341 A1 | 3/2006 | Cornish et al. |

FOREIGN PATENT DOCUMENTS

| | | | |
|---|---|---|---|
| GB | 1 274 492 | 5/1972 | |
| WO | WO 90/02757 | 3/1990 | ............. C07K 13/00 |
| WO | WO 99/15195 | 4/1998 | |
| WO | WO 98/21238 | 5/1998 | |
| WO | WO 00/9113 | 2/2000 | |
| WO | WO 01/62774 A2 | 8/2001 | ............... C07K 1/36 |

OTHER PUBLICATIONS

Anderiesz C et at. Effect of recombinant human gonadotrophins on human, bovine and murine oocyte meiosis, fertilization and embryonic development in vitro, Hum Reprod. May 2000;15(5):1140-8.*
Livestock Library http://www.livestocklibrary.com.au/handle/1234/6392?show=full Printed Jul. 27, 2013, pubilcation 1966 pp. 1-6.*
Bovine(2014) PDF Bovine—Definition and More from the Free Merriam-Webster Dictionary.*
Sheep(2014) PDF Sheep—Definition and More from the Free Merriam-Webster Dictionary.*
"Superovulation of Cattle, Medically Assisted Conception," in An Agenda for Research (1989), The National Academy of Sciences, pp. 131-132.
"Genetic Management of Breeding Colonies," in Rodents (1996), The National Academy of Sciences, pp. 35-43.
U.S. Appl. No. 60/380,043, filed May 2, 2002, Colgin.
U.S. Appl. No. 60/380,042, filed May 2, 2002, Colgin.
U.S. Appl. No. 60/377,987, filed May 2, 2002, Colgin.
U.S. Appl. No. 60/377,921, filed May 2, 2002, Colgin.
U.S. Appl. No. 60/377,829, filed May 2, 2002, Colgin.
U.S. Appl. No. 60/377,355, filed May 2, 2002, Colgin.
U.S. Appl. No. 60/377,166, filed May 2, 2002, Colgin.
U.S. Appl. No. 60/377,165, filed May 2, 2002, Colgin.
Bartolome, J.A. et al., "Comparison of synchronization of ovulation and induction of estrus as therapeutic strategies for bovine ovarian cysts in the dairy cow," (2000) Theriogenology 53(3):815-25 (abstract only).
Binelli, M. et al., "Antiluteolytic strategies to improve fertility in cattle," (2001)Theriogenology, 56:1451-1463.
Bo, GA et al. "Exogenous control of follicular wave emergence in cattle," (1995) Theriogenology 43:31-40.
Boime et al. (1992) "Expressions of Recombinant Human FSH, LH, and CG in Mammalian Cells: A Structure-Function Model for Therapeutic Drug Design," Seminars in Reprod. Endocrin. 10:45-50.
Chagas e Silva et al.,(2002) "Plasma progesterone profiles and factors affecting embryo-fetal mortality following embryon transfer in dairy cattle," Theriogenology 58(1):51-59 (abstract only).
Dematawewa, C.M., and P.J. Berger, "Genetic and phenotypic parameters for 305 day yield, fertility, and survival in Holsteins," 1998J. Dairy Sci., 81:2700-2709.
De Rensis, F. et al., "Fertility in postpartum dairy cows in winter or summer following estrus synchronization and fixed time AI after the induction of an LH surge with GnRH or hCG," (2002) Theriogenology 58(9):1675-1687 (abstract only).
Diaz et al. (1998) "Human Chorionic Gonadotropin-Induced Alterations in Ovarian Follicular Dynamics During the Estrous Cycle of Heifers," J. Anim. Sci. 76:1929-1936.
D'Occhio et al. (2000 "Reproductive Responses of Cattle to GnRH Agonists," Anim. Reprod. Sci. 60-61:433-442.
Eduvie and Seguin (1982) "Corpus Luteum Function and Pregnancy Rate in Lactating Dairy Cows Given Human Chrionic Gonadotropin at Middiestrus," Theriogenology 17:415-422.
Farin et al. (1988) "Effect of Luteinizing Hormone and Human Chorionic Gondotropin on Cell Populations in the Ovine Corpus Luteum," Biol. Reprod. 38:413-421.
Fray, MD et al. "Modulation of sex hormone secretion in cows by acute infection with bovine viral diarrhorea virus," (2002) Reproduction 123(2):281-289.
Grohn, Y.T. and P.J. Rajala-Schultz, "Epidemiology of reproductive performance in dairy cows," Anim. Repro. Sci., 60-61:605-614, 2000.
Gustafsson, H. and K. Larsson, "Embryonic mortality in heifers after artificial insemination and embryo transfer: differences between virgin and repeat breeder heifers," Res. Vet. Sci., 39:271-274, 1985.
Hansen, L.B., "Consequences of selection for milk yield from a geneticist's viewpoint," J. Dairy Sci., 83:1145-1150, 2000.
Helmer and Britt (1986) "Fertility of Dairy Cattle Treated with Human Chorionic Gonadotropin (hCG) to Stimulate Progesterone Secretion," Theriogenology 26:683-695.
Hoyer, P.B. and Niswender, G.D., "The regulation of steroidogenesis is different in the two types of ovine luteal cells," (1985) Can. J. Physiol. Pharmacol. 63(3):240-248 (abstract only).
Imwalle, D.B. et al. (1998) "Effects of melengestrol acetate on onset of puberty, follicular growth, and patterns of luteinizing hormone secretion in beef heifers" Biol. Repro. 58:1432-1436.
Juengel, J.L. and Niswender, G.D., "Molecular regulation of luteal progesterone synthesis in domestic ruminants," (1999) J. Reprod. Fertil. Suppl. 54:193-205 (abstract only).
Kaetzel (1985) "Expression of Biologically Active Bovine Luteinizing Hormone in Chinese Hamster Ovary Cells," PNAS USA 82:7280-7283.
Lee, C.N. et al., "Efficacy of gonadotropin-releasing hormone administered at the time of artificial insemination of heifers and postpartum and repeat breeder dairy cows," (1983) Am. J. Vet. Res. 44(11):2160-2163 (abstract only).
Lucy, M.C., "Reproductive loss in high-producing dairy cattle: Where will it end?," J. Dairy Sci., 84:1277-1293, 2001.
Lucy, M.C. et al., "Reproductive endocrinology of lactating dairy cows selected for increased milk production," J. Anim. Sci., 76 (Suppl. 1):#961 p. 246, 1998.
Macmillan, K.L. et al., "The effects of lactation on the fertility of dairy cows" Aust. Vet. J., 73:141-147, 1996.

(56) References Cited

OTHER PUBLICATIONS

Martinez, M.F. et al., "Effect of LH or GnRH on the dominant follicle of the first follicular wave in beef heifers," (1999) *Anim. Reprod. Sci.* 57:23-33.
Metzger et al. (1988) "The Human Oestrogen Receptor Functions in Yeast," *Nature*, 334: 31-36.
Moreira, F. et al. (2000) "Effect of day of the estrous cycle at the initiation of a timed insemination protocol on reproductive responses in dairy heifers," *J. Anim. Sci.* 78:1568-1576, 2000.
Nebel, R.L. and M.L. McGilliard, "Interactions of high milk yield and reproductive performance in dairy cows," *J. Dairy Sci.*, 76:3257-3268, 1993.
Nilson (1987) "Expression of the Genes Encoding Bovine LH in a Line of Chinese Hamster Ovary Cells," *J. Reprod. Fertil. Suppl.* 34:227-36.
Otieno et al., "Espression of luteinizing hormone genes in bovine conceptuses," (2002) *Reproduction* 123(1):155-162 (abstract only).
Pursley, J.R. et al., "Effect of time of artificial insemination on pregnancy rates, calving rates, pregnancy loss, and gender ratio after synchronization of ovulation in lactating dairy cows," (1998) *J. Dairy Sci.*, 81:2139-2144 (abstract only).
Pursley et al. (1997) "Reproductive Management of Lactating Dairy Cows Using Synchronization of Ovulation," *J. Dairy Sci.* 80(2):301-306.
Rajamahendran, R et al. "Effects of buserelin injection and deslorelin (GnRH-agonist) implants on plasma progesterone, LH, accessory CL formation, follicle and corpus luteum dynamics in Holstein cows," (1998) *Theriogenology* 50:1141-1155.
Roche, J.F. et al., "Reproductive management of postpartum cows," (2000) *Anim. Reprod. Sci.*, 60-61:703-712.
Royal, M.D. et al., "Declining fertility in dairy cattle: changes in traditional and endocrine parameters of fertility," (2000) *Anim. Sci.*, 70:487-502.
Sangsritavong, S. et al., "Liver blood flow and steroid metabolism are increased by both acute feeding and hypertrophy of the digestive tract," (2000) *J. Anim. Sci.*, 78(Suppl 1)#931 p. 221.
Santos et al., "Effect of human chorionic gonadotropin on luteal function and reproductive performance of high-producing lactating Holstein dairy cows," (2001) *J. Animal Science* 79:2881-2894.
Schmitt et al. (1996) "Differential Response of the Luteal Phase and Fertility in Cattle Following Ovulation of the First-Wave Follicle with Human Chorionic Gonadotropin or an Agonist of Gonadotropin-Releasing Hormone," *J. Anim. Sci.* 74:1074-1083.
Schmitt et al. (1996) "A Cellular and Endocrine Characterization of the Original and Induced Corpus Luteum After Administration of a Gonadotropin-Releaseing Hormone Agonist or Human Chorionic Gonadotropin on Day Five of the Estrous Cycle," *J. Anim. Sci.* 74:1915-1929.
Sianangama and Rajamahendran (1992) "Effect of Human Chorionic Gonadotropin Administered at Specific Times Following Breeding on Milk Progesterone and Pregnancy in Cows," *Theriogenology* 38:85-96.
Sianangama and Rajamahendran (1996) "Characteristics of Corpus Luteum Formed from the First Wave Dominant Follicle Following hCG in Cattle," *Theriogenology* 45:977-990.
Staples, C.R. et al., "Relationship between ovarian activity and energy status during the early postpartum period of high producing dairy cows," (1990) *J. Dairy Sci.*, 73:938-947.
Thatcher, W.W. et al., "Strategies to optimize reproductive efficiency by regulation of ovarian function," (Jul. 2002) *Domest. Anim. Endocrinol.* 23(1-2):243-54 (abstract only).
Thatcher, W.W. et al., "Effects of hormonal treatments in reproductive performance and embryo production," (2001) *Theriogenology* 55:75-89.
Vasconcelos JLM, et al., "Synchronization rate, size of the ovulatory follicle, and pregnancy rate after synchronization of ovulation beginning on different days of the estrous cycle in lactating dairy cows," (1999) *Theriogenology* 52: 1067-1078.
Vasconcelos, J.L.M. et al., "Reduction in size of the ovulatory follicle reduces subsequent luteal size and pregnancy rate," (2001) *Theriogenology*, 56:307-314.
Vasconcelos, J.L., et al., "Pregnancy rate, pregnancy loss, and response to heat stress after AI at 2 different times from ovulation in dairy cows" (1997) *Biol. Reprod.*, 56 (Supp.1):# 230 p. 140.
Weems et al. (1998) "Effect of Luteinizing Hormone (LH), PGE2, 8-EPI-PGE1, 8-EPI-PGE2, Trichosanthin, and Pregnancy Specific Protein B (PSPB) on Secretion of Progesterone In Vitro by Corpora Lutea (CL) from Nonpregnant and Pregnant Cows," *Prostaglandins & Other Lipid Mediators* 55:27-42.
Wiltbank, M.C. et al., "Novel effects of nutrition on reproduction in lactating dairy cows," (2001) *J. Dairy Sci.*, 84(Suppl. 1):#132,p. 32.
Wood, S.L., et al., "Improved synchrony of estrus and ovulation with the addition of GnRH to a melengestrol acetate-prostaglandin synchronization treatment in beef heifers," (2001) *J. Anim. Sci.* 79:2210-2216.
Wolfenson, D. et al., "Impaired reproduction in heat-stressed cattle: basic and applied aspects," (2000) *Anim. Reprod. Sci.*, 60-61:535-547.
De Araujo Berber, RC. et al. "Comparison of two Ovsynch protocols (GnRH versus LH) for fixed timed insemination in buffalo (*Bubalus bubalis*)"; *Theriogenology*, (2002) 57(5):1421-1430.
Gordon, U.D. et al. "A randomized prospective assessor-blind evaluation of luteinizing hormone dosage and in vitro fertilization outcome"; *Fertility and Sterility*, (2001) 75(2):324-330.
Martinez, M.F. et al. "The use of a progesterone-releasing device (CIDR-B) or melengestrol acetate with GnRH, LH, or estradiol benzoate for fixed-time AI in beef heifers"; (2002) 80:1746-1751.
de los Santos-Valadez et al. "Effect of hCG on Pregnancy Rates in Bovine Embryo Transfer Recipients," Theriogenology (1982) 17:85.
Hanlon et al. "Supplementing previously treated anestrous dairy cows with progesterone does not increase first-service conception rate," Theriogenology (2005) 63:239-245.
Holness et al. "Observations on the Use of Human Chorionic Gonadotrophin (HCG) During the Post-Insemination Period on Conception Rates in Synchronized Beef Cows with Sub-Optimum Reproductive Performances," Theriogenology (1982) 17:133-140.
Looney et al. "Pregnancy Rates Following HCG Administration at the Time of Transfer in Embryo-Recipient Cattle," Theriogenology (1984) 21:246.
Morris et al. "Peripheral Progesterone Levels in Pregnant and Non-pregnant Heifers Following Use of hCG," Theriogenology (1976) 6(4):367-378.
Rhodes et al. "Supplementing treated anoestrous dairy cows with progesterone does not increase conception rates," New Zealand Veterinary Journal (2001) 49(1):8-12 (Abstract only).
Banik, UK "Pregnancy-terminating Effect of Human Chorionic Gonadotropin in Rats"; *J Reprod Fertil*, (1975), 42(1):67-76.
Breuel, KF et al. "Firs-Service Pregnancy Rate in Beef heifers as Influenced by Human Chorionic Gnadotropin Administration Before and/or After Breeding"; *Theriogenology*, (1990), 34(1):139-45.
Campanile, G.et al. "Corpus luteum function and embryonic mortality in buffaloes treated with a GnRH agonist, hCG and progesterone"; *Theriogenology*, (2007), 67(8):1393-8.
Chagas e Silva. J. et al. "Luteotrophic influence of early bovine embryos and the relationship between plasma progesterone concentrations and embryo survival"; *Theriogenology*, (2005), 64(1):49-60.
Diskin, MG et al. "Effect of Progesterone Supplementation on Pregnancy and Embryo Survival in Ewes"; *J Anim Sci*, (1989), 67(6):1559-63.
Funston, RN et al. "Effect of administration of human chorionic gonadotropin after artificial insemination on concentrations of progesterone and conception rates in beef heifers"; *J Anim Sci*, (2005), 83(6):1403-5.
Hanlon, DW et al. "The effect of hCG administration five days after insemination on the first service conception rate of anestrous dairy cows"; *Theriogenology*, (2005), 63(7):1938-45.
Hansel, W et al. "Influence of Human Chorionic gonadotropin on Pregnancy Rates in Lactating Dairy and Beef Cows"; (*J Dairy Sci*, (1976) 59(4):751-4.

(56) References Cited

OTHER PUBLICATIONS

Helmer, SD et al. "Fertility of Dairy Cattle Treated with Human Chorionic Gonadotropin (hCG) to Stimulate Progesterone Secretion"; *Theriogenology*, (1986), 26(5):683-95.

Lewis, GS et al. "Effects of Gonadotropin-Releasing Hormone and Human Chroionic gonadotropin on Pregnancy Rate in Dairy Cattle"; *J Dairy Sci*, (1990), 73(1):66-72.

Nogueira, MFG et al. "Do high progesterone concentrations decrease pregnancy rates in embryo recipients synchronized with PGF2a and eCG"; *Theriogenology*, (2004), 61(7-8):1283-90.

Peters, AR "Embryo mortality in the cow"; *Animal Breeding Abstracts*, (1996), 64(8):587-598.

Schmit, EJ-P et al. "Differential Response of the Luteal Phase and Fertility in Cattle Following Ovulation of the First-Wave Follicle with Human Chorionic Gonadotropin or an Agonist of Gonadotropin-Releasing Hormone"; *J Anim Sci*, 1996, 74:1074-1083.

Stevenson and Mee "Pregnancy Rates of Holstein Cows After Postinsemination Treatment with a Progesterone-Releasing Intravaginal Device"; *Dairy Sci*, 1991, 74:3849-3856.

Stevenson, JS et al. "Maintenance of Pregnancy in Dairy Cattle After Treatment with Human chorionic gonadotropin or gonadotropin-Releasing Hormone"; *J Dairy Sci*, (2008), 91(8):3092-101.

Van Clee, J et al. "Effects of Administering Progesterone at Selected Intervals after Insemination of synchronized heifers on pregnancy Rates and resynchonization of Returns to Service"; *Theriogenology*, (1996), 46(7):1117-30.

Wagner, JF et al. "Effect of Placental Gonadotropin on Pregnancy Rate in the Bovine"; *J Anim Sci*, (1973), 36:1129-1136.

\* cited by examiner

SEQUENCE LISTING

<160> NUMBER OF SEQ ID NOS: 4

<210> SEQ ID NO 1
<211> LENGTH: 713
<212> TYPE: DNA
<213> ORGANISM: Bos taurus
<300> PUBLICATION INFORMATION:
<301> AUTHORS: Nilson,J.H., Thomason,A.R., Cserbak,M.T., Moncman,C.L.
      and Woychik,R.P.
<302> TITLE: Nucleotide sequence of a cDNA for the common alpha subunit
      of the bovine pituitary glycoprotein hormones. Conservation of
      nucleotides in the 3'-untranslated region of bovine and human
      pre-alpha subunit mRNAs
<303> JOURNAL: Journal of Biological Chemistry
<304> VOLUME: 258
<305> ISSUE: 8
<306> PAGES: 4679-4682
<307> DATE: 1983-04-25
<308> DATABASE ACCESSION NUMBER: GenBank/ X00050
<309> DATABASE ENTRY DATE: 1995-03-30
<313> RELEVANT RESIDUES: (98)..(661)
<300> PUBLICATION INFORMATION:
<301> AUTHORS: Erwin,C.R., Croyle,M.L., Donelson,J.E. and Maurer,R.A.
<302> TITLE: Nucleotide sequence of cloned complementary
      deoxyribonucleic acid for the alpha subunit of bovine pituitary
      glycoprotein hormones
<303> JOURNAL: Biochemistry
<304> VOLUME: 22
<305> ISSUE: 20
<306> PAGES: 4856-4860
<307> DATE: 1983-09-27
<308> DATABASE ACCESSION NUMBER: GenBank/ X00050
<309> DATABASE ENTRY DATE: 1995-03-30
<313> RELEVANT RESIDUES: (1)..(713)
<300> PUBLICATION INFORMATION:
<308> DATABASE ACCESSION NUMBER: X00050

<309> DATABASE ENTRY DATE: 1995-03-30
<313> RELEVANT RESIDUES: (1)..(713)

<400> SEQUENCE: 1

| | | | | | |
|---|---|---|---|---|---|
| aaaaactaaa | attcttcttc | agatccacag | tcaactgccc | tgactacatt ctgcaaaaat | 60 |
| ccagaggacg | aagagccatg | gattactaca | gaaaatatgc | agctgtcatt ctgaccattt | 120 |
| tgtctctgtt | tctgcaaatt | ctccattcct | ttcctgatgg | agagtttaca atgcagggct | 180 |
| gtcctgaatg | caagctaaaa | gaaaacaaat | acttctccaa | gccagatgct gcaatctatc | 240 |
| agtgcatggg | gtgctgcttc | tccagggcat | accccactcc | agcgaggtct aagaagacaa | 300 |
| tgttggtccc | caagaacatc | acctcggaag | ctacatgctg | tgtggccaaa gcatttacca | 360 |
| aggccacagt | gatgggaaat | gtcagagtgg | agaaccacac | cgagtgccac tgcagcactt | 420 |
| gttattatca | caaatcctaa | tagtttgcag | tgggccttgc | tgatgatggc tgacttgctc | 480 |
| aaaaggaaaa | ttaatttgtc | cagtgtctat | ggctttgtga | gataaaaccc tccttttcct | 540 |
| tgccatacca | tttttaacct | gctttgagaa | tatactgcag | ctttattgct tttctcctta | 600 |
| tcctacaata | taatcagtag | tcttgatctt | ttcatttgga | atgaaatatg gcatttagca | 660 |
| tgaccataaa | aagctgattc | cactggaaat | aaagtctttt | aaatcatcac tct | 713 |

<210> SEQ ID NO 2
<211> LENGTH: 629
<212> TYPE: DNA
<213> ORGANISM: Bos taurus
<300> PUBLICATION INFORMATION:
<301> AUTHORS: Maurer,R.A.
<302> TITLE: Analysis of several bovine lutropin beta subunit cDNAs reveals heterogeneity in nucleotide sequence
<303> JOURNAL: Journal of Biological Chemistry
<304> VOLUME: 260
<305> ISSUE: 8
<306> PAGES: 4684-4687
<307> DATE: 1985-04-25
<308> DATABASE ACCESSION NUMBER: GenBank/M10077
<309> DATABASE ENTRY DATE: 1993-04-27
<313> RELEVANT RESIDUES: (1)..(629)
<300> PUBLICATION INFORMATION:
<308> DATABASE ACCESSION NUMBER: GenBank/M1007
<309> DATABASE ENTRY DATE: 1993-04-27
<313> RELEVANT RESIDUES: (1)..(629)

<400> SEQUENCE: 2

| | | | | | |
|---|---|---|---|---|---|
| gatgttccag | ggactgctgc | tgtggctgct | gctgggcgtg | gccggggtgt gggcttccag | 60 |
| ggggccactg | cggccgctgt | gccagcccat | caacgccacc | ctggcggctg agaaggaggc | 120 |
| ctgccctgtc | tgtatcactt | tcaccaccag | catctgcgcc | ggctactgcc ccagcatgaa | 180 |
| gcgggtgctg | cctgtcatcc | tgccgcccat | gccccagcgg | gtgtgcacct accatgagct | 240 |
| gcgcttcgcc | tccgttcggc | tccccggctg | cccacctgga | gtggacccaa tggtctcctt | 300 |
| ccccgtggcc | ctcagctgtc | actgtggatc | ctgccgcctc | agcagcactg actgcggggg | 360 |
| tcccagaacc | caaccttgg | cctgtgacca | ccccgctc | ccagacatcc tcttcctcta | 420 |
| aggatgcccc | acttcaacct | cccatgccca | tcctaactct | ggaaaccagc agacactctt | 480 |
| ccctcccctt | cccaataaag | acttctcaaa | ctgcctaggc | tggcctaata ataattgtaa | 540 |
| tcattattaa | cccagaagtt | cttcaaatat | aagattaaaa | agatgaacag atataattct | 600 |
| taccccttatt | aaagacaaaa | gagttttct | | | 629 |

<210> SEQ ID NO 3
<211> LENGTH: 731
<212> TYPE: DNA

<213> ORGANISM: Bos taurus
<300> PUBLICATION INFORMATION:
<301> AUTHORS: Goodwin,R.G., Moncman,C.L., Rottman,F.M. and Nilson,J.H.
<302> TITLE: Characterization and nucleotide sequence of the gene for
       the common alpha subunit of the bovine pituitary glycoprotein
       hormones
<303> JOURNAL: Nucleic Acids Research
<304> VOLUME: 11
<305> ISSUE: 19
<306> PAGES: 6873-6882
<307> DATE: 1983-10-11
<308> DATABASE ACCESSION NUMBER: GenBank/NM_173901
<309> DATABASE ENTRY DATE: 2003-12-22
<313> RELEVANT RESIDUES: (1)..(731)
<300> PUBLICATION INFORMATION:
<301> AUTHORS: Erwin,C.R., Croyle,M.L., Donelson,J.E. and Maurer,R.A.
<302> TITLE: Nucleotide sequence of cloned complementary
       deoxyribonucleic acid for the alpha subunit of bovine pituitary
       glycoprotein hormones
<303> JOURNAL: Biochemistry
<304> VOLUME: 22
<305> ISSUE: 20
<306> PAGES: 4856-4860
<307> DATE: 1983-09-27
<308> DATABASE ACCESSION NUMBER: GenBank/NM_173901
<309> DATABASE ENTRY DATE: 2003-12-22
<313> RELEVANT RESIDUES: (1)..(731)
<300> PUBLICATION INFORMATION:
<308> DATABASE ACCESSION NUMBER: GenBank/NM_173901
<309> DATABASE ENTRY DATE: 2003-12-22
<313> RELEVANT RESIDUES: (1)..(731)

<400> SEQUENCE: 3

```
gcagttgctg agaaatcaca agacaaaact aaaattcttc ttcagatcca cagtcaactg     60
ccctgactac attctgcaaa atccagagg acgaagagcc atggattact acagaaaata    120
tgcagctgtc attctggcca ttttgtctct gtttctgcaa attctccatt cctttcctga   180
tggagagttt acaatgcagg gctgtcctga atgcaagcta aaagaaaaca aatacttctc   240
caagccagat gctccaatct atcagtgcat ggggtgctgc ttctccaggg catacccccac  300 tccagcgagg tctaagaaga caatgttggt ccccaagaac atcacctcgg aagctacatg   360
ctgtgtggcc aaagcattta ccaaggccac agtgatggga aatgtcagag tggagaacca   420
caccgagtgc cactgcagca cttgttatta tcacaaatcc taatagtttg cagtgggcct   480
tgctgatgat ggctgacttg ctcaaaagga aaattaattt gtccagtgtc tatggctttg   540
tgagataaaa ccctcctttt ccttgccata ccattttaa cctgctttga gaatatactg   600
cagctttatt gcttttctcc ttatcctaca atataatcag tagtcttgat cttttcattt    660
ggaatgaaat atggcattta gcatgaccat aaaaagctga ttccactgga ataaagtct    720 tttaaatcat c                                                        731
```

<210> SEQ ID NO 4
<211> LENGTH: 426
<212> TYPE: DNA
<213> ORGANISM: Bos taurus
<300> PUBLICATION INFORMATION:
<301> AUTHORS: Virgin,J.B., Silver,B.J., Thomason,A.R. and Nilson,J.H.
<302> TITLE: The gene for the beta subunit of bovine luteinizing hormone
       encodes a gonadotropin mRNA with an unusually short
       5'-untranslated region
<303> JOURNAL: Journal of Biological Chemistry
<304> VOLUME: 260
<305> ISSUE: 11
<306> PAGES: 7072-7077
<307> DATE: 1985-06-10
<308> DATABASE ACCESSION NUMBER: GenBank/NM_173930
<309> DATABASE ENTRY DATE: 2003-12-22
<313> RELEVANT RESIDUES: (1)..(426)
<300> PUBLICATION INFORMATION:

```
<301> AUTHORS: Maurer,R.A.
<302> TITLE: Analysis of several bovine lutropin beta subunit cDNAs
      reveals heterogeneity in nucleotide sequence
<303> JOURNAL: Journal of Biological Chemistry
<304> VOLUME: 260
<305> ISSUE: 8
<306> PAGES: 4684-4687
<307> DATE: 1985-04-25
<308> DATABASE ACCESSION NUMBER: GenBank/NM_173930
<309> DATABASE ENTRY DATE: 2003-12-22
<313> RELEVANT RESIDUES: (1)..(426)
<300> PUBLICATION INFORMATION:
<308> DATABASE ACCESSION NUMBER: GenBank/NM_173930
<309> DATABASE ENTRY DATE: 2003-12-22
<313> RELEVANT RESIDUES: (1)..(426)

<400> SEQUENCE: 4
atggagatgt tccagggact gctgctgtgg ctgctgctgg gcgtggccgg ggtgtgggct      60
tccagggggc cactgcggcc gctgtgccag cccatcaacg ccaccctggc ggctgagaag     120
gaggcctgcc ctgtctgtat cactttcacc accagcatct gcgccggcta ctgccccagc     180
atgaagcggg tgctgcctgt catcctgccg cccatgcccc agcgggtgtg cacctaccat     240
gagctgcgct tcgcctccgt tcggctcccc ggctgcccac ctggagtgga cccaatggtc     300
tccttccccg tggccctcag ctgtcactgt ggacccgcc gcctcagcag cactgactgc     360
gggggtccca gaacccaacc cttggcctgt gaccacccc cgctcccaga catcctcttc     420
ctctaa                                                                426
```

METHODS AND KITS FOR MAINTAINING PREGNANCY, TREATING FOLLICULAR CYSTS, AND SYNCHRONIZING OVULATION USING LUTEINIZING HORMONE

CROSS-REFERENCE TO RELATED APPLICATIONS

This application claims priority to U.S. Provisional Applications 60/452,297 filed Mar. 4, 2003 and 60/516,002 filed Oct. 31, 2003, both of which are incorporated herein by reference to the extent not inconsistent with the disclosure herewith.

BACKGROUND OF THE INVENTION

There are over nine million dairy cows in the United States, over one million in Canada and over fifty million worldwide. The dairy industry is extremely competitive and the ability of a dairy to maintain pregnancies post insemination is critical to the profitability of the producer. It is estimated that the cost of a non-pregnant cow is about five dollars per day. It is further estimated that current inseminations result in approximately thirty to forty percent pregnant cows at day 45 and of those cows ninety to ninety-five percent deliver calves at the end of the 283-day gestation period. Reproductive efficiency in dairy cattle has been declining steadily over a prolonged period of time. The magnitude and the consistency of this trend are of great importance to the dairy industry and amount to a steady decline of approximately one percent in first service conception rates per year for the last ten years. The impact of this change in productivity has not been readily apparent, because individual cow milk production has increased by twenty percent over the same period. In the long run, the dairy industry cannot afford to continue the current rate of declining reproductive performance.

The primary revenue source in the dairy industry is milk production. Progress in genetics and management of dairy cows has led to remarkable increases in milk production throughout the last several decades, with a twenty percent increase in per-cow production in the last ten years alone (USDA National Agricultural Statistics Service, http//www.usda.gov/nass). In order to maintain high herd productivity, however, cows must become pregnant and deliver a calf so that the lactation cycle is renewed. Additionally, sufficient numbers of heifers must be produced to replace older cows. Therefore, the future productivity of the dairy industry is very dependent on the maintenance of fertility and reproduction.

During the same time that milk production per cow has increased, however, reproductive efficiency of dairy cows has steadily declined. Colorado dairy herds are among the most productive in the nation, and the state currently ranks second in average yearly per-cow production (USDA National Agricultural Statistics Service, http//www.usda.gov/nass). The Colorado dairy industry is typical for the national trend in declining cow fertility. From 1992 through the present, while milk production has increased from 21,000 to 24,000 lbs/cow/yr, average days open (days until conception) have increased from 130 to 173 days. The first service conception rate for Colorado herds has declined from 51% to 37%, and the rate of services per conception has risen from 2 to 2.8 during the last 10 years (data from Dairy Herd Improvement Association, www.dhiprovo.com).

Declining reproductive efficiency of dairy cattle has been observed throughout the United States, and other parts of the world where milk production has been increasing (Lucy, M. C., "Reproductive loss in high-producing dairy cattle: Where will it end?," *J. Dairy Sci.*, 84:1277-1293, 2001; Roche, J. F. et al., "Reproductive management of postpartum cows," *Anim. Reprod. Sci.*, 60-61:703-712, 2000; Royal, M. D. et al., "Declining fertility in dairy cattle: changes in traditional and endocrine parameters of fertility," *Anim. Sci.*, 70:487-502, 2000; and Macmillan, K. L. et al., "The effects of lactation on the fertility of dairy cows" *Aust. Vet. J*, 73:141-147, 1996). The strong temporal association between increasing milk production and decreasing fertility does not provide a known cause of the phenomenon. While the relationship between milk production and fertility appears to be antagonistic (Dematawewa, C. M., and P. J. Berger, "Genetic and phenotypic parameters for 305 day yield, fertility, and survival in Holsteins," *J. Dairy Sci.*, 81:2700-2709, 1998; and Hansen, L. B., "Consequences of selection for milk yield from a geneticist's viewpoint," *J. Dairy Sci.*, 83:1145-1150, 2000), some studies demonstrate a neutral effect of milk production per se (Grohn, Y. T. and P. J. Rajala-Schultz, "Epidemiology of reproductive performance in dairy cows," *Anim. Repro. Sci.*, 60-61:605-614, 2000), and other studies show higher producing herds have better reproductive performance than lower producing herds (Nebel, R. L. and M. L. McGilliard, "Interactions of high milk yield and reproductive performance in dairy cows," *J. Dairy Sci.*, 76:3257-3268, 1993; and Stevenson, J. S., "Can you have good reproduction and high milk yield?" *Hoard's Dairyman*, 145:202-203, 1999). Numerous features of high producing cows may negatively influence fertility, including negative energy balance and disease events such as retained placenta, ketosis, cystic ovary, and mastitis (Lucy 2001, supra; Grohn 2000, supra; and Staples, C. R. et al., "Relationship between ovarian activity and energy status during the early postpartum period of high producing dairy cows," *J. Dairy Sci.*, 73:938-947, 1990). A prominent trend in the U.S. dairy industry is decreased number of dairy farms, steadily increasing herd size, and movement of dairy production to the western states (USDA National Agricultural Statistics Service, http//www.usda.gov/nass). Larger herd size may contribute to decreased reproductive performance because of the associated changes in the dairy labor force and cow management, resulting in poorly trained or over tasked workers identifying estrus behavior, performing artificial insemination, conducting estrus synchronization programs, and identifying and treating sick cows (Lucy 2001, supra). Heat stress, which occurs throughout much of the year in western and southwestern US dairy herds, has significant negative impact on cattle fertility (Wolfenson, D. et al., "Impaired reproduction in heat-stressed cattle: basic and applied aspects," *Anim. Reprod. Sci.*, 60-61:535-547, 2000).

Recent studies with ultrasonic pregnancy detection demonstrate embryonic losses of at least 20% between 28 and 60 days of pregnancy (Pursley, J. R. et al., "Effect of time of artificial insemination on pregnancy rates, calving rates, pregnancy loss, and gender ratio after synchronization of ovulation in lactating dairy cows," *J. Dairy Sci.*, 81:2139-2144, 1998; and Vasconcelos, J. L., et al., "Pregnancy rate, pregnancy loss, and response to heat stress after AI at 2 different times from ovulation in dairy cows" *Biol. Reprod.*, 56 (Supp. 1):140, 1997), and there are likely even higher losses prior to 28 days that are undetected by ultrasound examination (Lucy 2001, supra). Data suggest that modern dairy cows fail to establish pregnancy because of suboptimal uterine environment (Gustafsson, H. and K. Larsson, "Embryonic mortality in heifers after artificial insemination and embryo transfer: differences between virgin and repeat breeder heifers," *Res. Vet. Sci.,* 39:271-274, 1985). Although there are numerous possible factors that could be responsible for embryonic losses, one potential cause is low blood progesterone concentration.

Progesterone is required to maintain pregnancy in cattle, and low progesterone concentrations are associated with infertility. Blood progesterone concentrations are influenced by rates of secretion and metabolism/clearance. There is evidence that modern dairy cows maintain lower blood progesterone concentrations than those measured in cattle several decades ago (Lucy, M. C. et al., "Reproductive endocrinology of lactating dairy cows selected for increased milk production," *J. Anim. Sci.,* 76 (Suppl. 1):296, 1998). Larger corpora lutea secrete more progesterone and have a positive effect on pregnancy recognition and pregnancy rates, but there is evidence that dairy cows have smaller than desirable corpora lutea in some circumstances (Lucy 2001, supra; Vasconcelos, J. L. M. et al., "Reduction in size of the ovulatory follicle reduces subsequent luteal size and pregnancy rate," *Theriogenology,* 56:307-314, 2001). The liver is the primary site of progesterone metabolism. Recent studies show that increased feed intake increases liver blood flow and increases the rate of progesterone clearance, thus decreasing serum progesterone concentrations (Sangsritavong, S. et al., "Liver blood flow and steroid metabolism are increased by both acute feeding and hypertrophy of the digestive tract," *J. Anim. Sci.,* 78(Suppl 1)221, 2000; and Wiltbank, M. C. et al., "Novel effects of nutrition on reproduction in lactating dairy cows," *J. Dairy Sci.,* 84(Suppl. 1):84, 2001).

Low serum progesterone during the luteal phase of the estrus cycle would be associated with low first service conception rate. Low progesterone concentrations may result from inadequate secretion, or alternatively high levels of metabolism/clearance, even when insemination has produced a potentially viable embryo. Low progesterone would allow the generation of prostaglandin by uterine endometrium at around day 16 of the estrus cycle, resulting in luteolysis and induction of ovulation, thus embryonic death and failure to maintain the pregnancy (Binelli, M. et al., "Antiluteolytic strategies to improve fertility in cattle," *Theriogenology,* 56:1451-1463, 2001).

Binelli et al. 2001, supra, reviews antiluteolytic strategies for improving fertility in cattle.

In cows, the estrus cycle is about 21 days. To determine when a cycling cow is ready for breeding, the cow can be observed for behavioral estrus. Alternatively, a cow can be induced or forced into estrus with effective hormone therapies. Estrus of an entire herd can be synchronized (U.S. Pat. No. 3,892,855 issued Jul. 1, 1975, and U.S. Pat. No. 4,610,687 issued Sep. 9, 1986; U.S. Patent Application No. 60/380,042; Wilson, T. W., "Estrous Synchronization for Beef Cattle," (June 2003), Bulletin 1232, the University of Georgia College of Agricultural and Environmental Sciences and the U.S. Department of Agriculture cooperating). Estrus synchronization, or preferably ovulation synchronization, is used in timed artificial insemination (TAI) breeding programs. TAI breeding programs involve precise estrus synchronization, which allows for timed breeding without monitoring for behavioral estrus. Examples of methods for forcing estrus include U.S. Pat. No. 5,589,457 (issued Dec. 31, 1996), Ovsynch (Pharmacia Animal Health, Peapack, N.J.), Cosynch, Select Synch, Modified Select Synch, MGA/PGF, and Syncro-Mate-B. Such methods typically employ hormones such as prostaglandins, e.g. PGF2α (Lutalyse®, Pharmacia Upjohn, Peapack, N.J.; Bovilene®, Syntex; Animal Health, Des Moines, Iowa; and Estrumate® Haver Lockhart, Shawnee, Kans.), and gonadotropin releasing hormone (GnRH). Ovsynch involves a GnRH injection followed by a prostaglandin injection one week later, followed by a second GNRH injection 48 hours later. Insemination is ideally then performed at 12-18 hours, preferably about 16 hours, after the second GNRH injection. Ovsynch is maximally effective when implemented between Days 18-20 of a 20-day bovine estrus cycle (Thatcher, W. W. et al. (2000) "New Strategies to Increase Pregnancy Rates" www.naab-css.org/education/Thatcher.html). Presynch (Pharmacia Animal Health, Peapack, N.J.) can be used to synchronize heifers before implementing Ovsynch. Ovsynch is maximally effective when implemented between Days 18-20 of a 20-day bovine estrus cycle (studies show starting between day 5-12 is best. (Moreira, F. et al. (2000) "Effect of day of the estrous cycle at the initiation of a timed insemination protocol on reproductive responses in dairy heifers," J Anim Sci 78:1568-1576, 2000; Vasconcelos J L M, et al. (1999) "Synchronization rate, size of the ovulatory follicle, and pregnancy rate after synchronization of ovulation beginning on different days of the estrous cycle in lactating dairy cows," Theriogenology 52: 1067-1078, 1999). Presynch involves two prostaglandin injections. Certain of the above-mentioned methods are also used on non-cycling cows to induce cycling, such as in lactating dairy cows. However, these protocols do not induce cyclicity—only progesterone priming does that. The only synchronization program that does induces cyclicity in lactating cows is using a controlled internal drug release device (CIDR) which releases progesterone or melengestrol acetate (MGA), which is illegal in lactating dairy cows). After precise estrus synchronization, animals need not be monitored for behavioral estrus and may be bred by appointment. Some animals may need estrus presynchronization before estrus synchronization. Melengestrol acetate (MGATM) in feed (Imwalle, D. B. et al. (1998) "Effects of melengestrol acetate on onset of puberty, follicular growth, and patterns of luteinizing hormone secretion in beef heifers" Biol. Repro. 58:1432-1436) or implants (U.S. Patent Publication No. 2001/0041697, published Nov. 15, 2001) can be used for presynchronizing estrus in heifers. Resynch is a program whereby animals are synchronized and bred, and then those animals that are determined to be open (not pregnant) are again synchronized and rebred.

Previous research has shown conflicting results on reproductive cycles and conception rates of cows receiving hCG (Eduvie and Seguin (1982) Theriogenology 17:415-422; Helmer and Britt (1986) Theriogenology 26:683-695; Sianangama and Rajamahendran (1992) Theriogenology 38:85-96; Diaz et al. (1998) J. Anim. Sci. 76:1929-1936; Sianangama and Rajamahendran (1996) Theriogenology 45:977-990; Schmitt et al. (1996) J. Anim. Sci. 74:1074-1083; and Schmitt et al. (1996) J. Anim. Sci. 74:1915-1929).

Thatcher et al. (2001 Theriogenology 55:75-89) describes the effects of hormonal treatments on the reproductive performance of cattle. Hormonal treatments include administration of bovine somatotrophin (bST) and hCG. D'Occhio et al. (2000 Anim. Reprod. Sci. 60-61:433-442) describes various strategies for beef cattle management using GNRH agonist implants. De Rensis et al. (2002 Theriogenology 58(9):1675-1687) describes the effect on dairy cows of administering GNRH or hCG before artificial insemination. Martinez et al. (1999 *Anim. Reprod. Sci.* 57:23-33) describes the ability of porcine luteinizing hormone (LH) and gonadotropin releasing hormone (GNRH) to induce follicular wave emergence in beef heifers on Days 3, 6, and 9 of the estrus cycle, after ovulation (Day 0), without insemination. Santos et al. (2001 J. Animal Science 79:2881-2894) describes the effect on reproductive performance of intramuscular administration of 3,300 IU of human chorionic gonadotropin (hCG) to high-producing dairy cows on Day 5 after artificial insemination. Lee et al. (1983 Am. J. Vet. Res. 44(11):2160-2163) describes the effect on dairy cows of administering GNRH at the time of artificial insemination (AI). U.S. Pat. No. 5,792,785 (issued Aug. 11, 1998) and U.S. Pat. No. 6,403,631 (issued Jun. 11, 2002) describe methods and compositions for administering melatonin before and after insemination to enhance pregnancy success in an animal. Chagas e Silva et al. (2002 Theriogenology 58(1):51-59) describes plasma progesterone profiles following embryo transfer in dairy cattle. Weems et al. (1998 Prostaglandins and other Lipid Mediators) describes the effects of hormones on the secretion of progesterone by corpora lutea (CL) from non-pregnant and pregnant cows. U.S. Pat. No. 4,780,451 (issued Oct. 25, 1988) describes compositions and methods using LH and follicle stimulating hormone (FSH) to produce superovulation in cattle Farin et al. (1988 Biol. Reprod. 38:413-421) describes the effect on ovine luteal weight of intravenous administration of 300 IU of hCG on Days 5 and 7.5 of the estrus cycle, without insemination. Hoyer and Niswender (1985 Can. J. Physiol. Pharmacol. 63(3):240-248) describe the regulation of steroidogenesis in ovine luteal cells. Juengel and Niswender (1999 J. Reprod Fertil. Suppl. 54:193-205) describe the molecular regulation of luteal progesterone in domestic ruminants. U.S. Pat. No. 5,589,457 (issued Dec. 31, 1996) describes methods for synchronizing ovulation in cattle using GNRH, LH, and/or hCG and PGF2α.

The gonadotropins form a family of structurally related glycoprotein hormones. Members include chorionic gonadotropin (CG), follicle-stimulating hormone (FSH), luteinizing hormone (LH), also known as lutropin, and thyroid stimulating hormone (TSH). FSH, LH, and TSH are present in most vertebrate species and are synthesized by the pituitary gland. CG has only been found in primates, including humans, and in horses, and is synthesized by placental tissues. The gonadotropins are heterodimers of two subunits, α and β, which are associated with non-covalent bonds. Within a species, the α subunit is essentially identical for each member of the gonadotropin family. The β subunits are different for each member, but are similar in structure. The β subunit of hCG is substantially larger than the other β subunits, in that is contains an additional 34 amino acids at the C-terminal end of the protein.

The effects of LH depend on the sex of the organism. In sexually mature females, LH stimulates the follicle to secrete estrogen in the first half of the menstrual cycle. A surge of LH triggers the completion of meiosis I of the egg and release of the egg (ovulation) in the middle of the cycle stimulates the now-empty follicle to develop into the corpus luteum, which secretes progesterone during the latter half of the menstrual cycle. In males, LH acts on the interstitial cells of the testes stimulating them to synthesize and secrete the male sex hormone testosterone. LH in males is also known as interstitial cell stimulating hormone (ICSH).

Production of recombinant bovine LH is described in WO 90/02757 (published Mar. 22, 1990), U.S. Pat. No. 6,455,282 (issued Sep. 24, 2002); U.S. Pat. No. 5,639,639 (issued Jun. 17, 1997), U.S. Pat. No. 5,767,251 (issued Jun. 16, 1998), Nilson (1987) J. Reprod. Fertil. Suppl. 34:227-36, Boime et al. (1992) Seminars in Reprod. Endocrin. 10:45-50, and Kaetzel (1985) PNAS USA 82:7280-7283. A process for the purification of recombinant LH is described in WO 01/62774 (published Aug. 30, 2001). U.S. Pat. No. 5,929,028 (issued Jul. 27, 1999) describes liquid gonadotropin containing formulations that may include LH. Otieno et al. (2002 Reproduction 123(1):155-162) describes expression of LH genes in bovine conceptuses.

There is a need in the art for a safe therapeutic for maintaining pregnancy of post-inseminated cows.

All publications and patent applications cited herein are incorporated herein by reference in their entirety to the extent that they are not inconsistent with the disclosure herein. Citation of the above documents is not intended as an admission that any of the foregoing is pertinent prior art. All statements as to the date or representation as to the contents of these documents is based on subjective characterization of the information available to the applicant, and does not constitute any admission as to the accuracy of the dates or contents of these documents.

SUMMARY OF THE INVENTION

This invention provides methods and kits for maintaining pregnancy in mammals. Pregnancy is maintained by administration of effective amounts of luteinizing hormone (LH) or chorionic gonadotropin (CG). Both LH and CG may be used alone, in combination with each other, or in combination with growth hormone (GH) or follicle stimulating hormone (FSH). Hormones are administered on about Day 4 to about Day 7 following insemination. Effective amounts of LH range from about 10 micrograms to about 25 milligrams and of CG range from about 100 IU (international units) to about 2000 IU. Mammals treatable by the methods of this invention include ungulates and related mammals, including bovines. Kits provided by this invention include effective amounts of one or more hormones, a device for administering the hormone(s) and instructions.

This invention also provides a method of synchronizing ovulation in a herd of female animals said method comprising: administering luteinizing hormone to the animals of said herd, preferably by intramuscular injection. Synchronizing ovulation may synchronize estrus; however, the animals can be bred, e.g., by artificial insemination, without signs of estrus being observed. Preferably, luteinizing hormone is used in an art-known estrus synchronization method instead of gonadotropin releasing hormone (GnRH). In typical synchronization protocols, about 100 mg gonadotropin is used. A number of art-known estrus synchronization methods are described in the Detailed Description hereof. Preferably, the amount of luteinizing hormone administered is between about 2 mg and about 10 mg. These methods induce ovulation more reliably than estrus synchronization methods using GnRH; however, a combination of luteinizing hormone and GnRH may also be used, e.g., in any ratio of luteinizing hormone to GNRH between about 99:1 to 1:99, preferably the ratio used is between about 25:75 and about 75:25.

Some estrus synchronization methods involve administering prostaglandin to said animals in an amount between about 25 mg and about 35 mg following administration of GnRH. Luteinizing hormone (or a mixture of luteinizing hormone and GNRH) may be used instead of GNRH in these methods, in the dosages described in the preceding paragraph. Other estrus synchronization methods involve administering GNRH, and then prostaglandin, and then additional GNRH; and again, luteinizing hormone (or a mixture of luteinizing hormone and GNRH) may be used instead of GNRH in these methods in the dosages described in the preceding paragraph. The timing of administration of luteinizing hormone and prostaglandin in these ovulation synchronization methods is as described in the art for the timing of administration of GnRH and prostaglandin in estrus synchronization methods. Preferably prostaglandin is administered between about 6 and about 8 days, and preferably about 7 days after administration of the first luteinizing hormone, i.e., a time sufficient to cause regression of the dominant follicle, Preferably, a second dose of luteinizing hormone is administered between about 40 and about 60 hours, and preferably about 48 hours after administration of prostaglandin, i.e., a time sufficient to allow sufficient maturation of the follicle to produce an ovary of good quality, but not so long as to allow the animal to spontaneously ovulate (since breeding should be done before ovulation).

The synchronization methods of this invention may also comprise breeding the animals by any means known to the art, preferably by artificial insemination. Breeding may be done immediately after administration of the final dose of hormone; i.e., within a one-day period, and preferably within about 16 hours, so that breeding can be accomplished before ovulation occurs.

The ovulation synchronization methods of this invention may be applied to animals selected from the group consisting of bovine, sheep, goats, yaks, water buffaloes, bison, antelopes, gazelles, elk, reindeer, moose, bighorn sheep, giraffes, and camelids including Bactrian and dromedary camels, llamas, swine, horses, alpacas, and vicunas. Preferably the animal is a bovine.

The ovulation synchronization methods of this invention may be used in combination with presynchronization methods known to the art.

This invention also provides a method for treating follicular cyst in a mammal comprising administering to a mammal diagnosed with a follicular cyst an effective amount of luteinizing hormone. Luteinizing hormone is preferably administered intramuscularly, and in an amount between about 2 and about 10 mg. Again, the treatment may be applied to a mammal selected from the group consisting of bovine, sheep, goats, yaks, water buffaloes, bison, antelopes, gazelles, elk, reindeer, moose, bighorn sheep, giraffes, and camelids including Bactrian and dromedary camels, llamas, swine, horses, alpacas, and vicunas, preferably bovine.

Recombinant luteinizing hormone may be used in any of the methods of this invention. Recombinant luteinizing hormone may be made by any means known to the art, and may be made by novel methods described herein. Recombinant luteinizing hormone is more effective at lower doses than luteinizing hormone purified from pituitary glands because it is more uniformly properly glycosylated. The amount of glycosylation depends on the stage of production of luteinizing hormone in the pituitary gland from which the hormone is being harvested. Typically, the hormone is harvested from pituitary glands at all stages of hormone production. Luteinizing hormone which is under-glycosylated has a shorter half life than luteinizing hormone which is properly glycosylated. Therefore, recombinant luteinizing hormone which is properly glycosylated may be used in lower dosages than isolated naturally-occurring luteinizing hormone.

One method of producing recombinant luteinizing hormone comprises expressing DNA encoding for said luteinizing hormone in insect cells. Recombinant LH can also be produced through the use of transgenic non-human animals, as in known in the art. A further useful method of producing recombinant LH comprises using a vector in which the alpha and beta subunits of luteinizing hormones are fused under the control of a single promoter. Methods of making recombinant LH may include "dual expression methods," which means the alpha and beta subunits are expressed from the same plasmid or viral DNA. In that case they are under the control of separate promoters on the same DNA molecule. The methods may use "co-expression," which means that the alpha and beta subunits are encoded by separate DNA molecules (each having a different antibiotic resistance gene). To accomplish co-expression, two separate plasmids are introduced into a cell line (mammalian or insect). The cell line is treated with two antibiotics to select for a cell line that contains both plasmids. Another method of making recombinant LH comprises expressing DNA encoding single-chain forms of LH, where the alpha and beta subunits are covalently linked.

This invention also provides an injection device for administering a single dose of recombinant luteinizing hormone, wherein said dose comprises between about 2 and about 10 mg recombinant luteinizing hormone. The injection device may be part of a kit which also includes such components as injection devices for administering single doses of other hormones required for ovulation synchronization, and pregnancy assays.

REFERENCE TO SEQUENCE LISTINGS

SEQ ID NO: 1 is bovine LH alpha from Genbank Accession Number X00050.

SEQ ID NO:2 is bovine LH beta from Genbank Accession Number M10077.

SEQ ID NO:3 is the nucleotide sequence for bovine LH alpha subunit from Genbank Accession Number NM_173901

SEQ ID NO:4 is the nucleotide sequence for bovine LH beta subunit from Genbank Accession Number NM_173930.

DETAILED DESCRIPTION OF THE INVENTION

Figure 1:
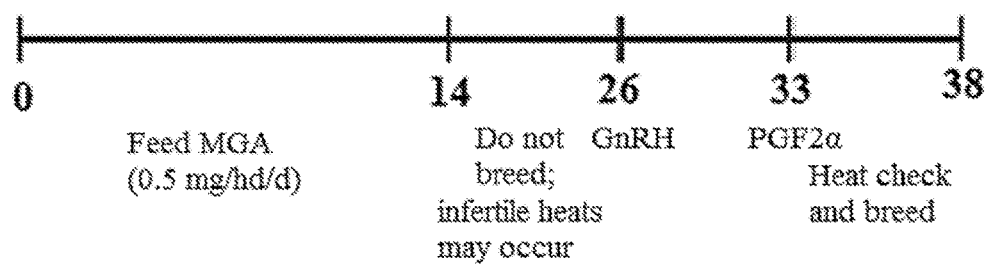
FIG. 1 illustrates a timeline for an MGA/GnRH/PGF$_{2\alpha}$estrus synchronization system.

As used herein, "ready for breeding" refers to an animal that is not pregnant. The animal may have been monitored for estrus and had estrus detected. The animal may have had estrus forced.

As used herein, "cow" refers to female bovines, including heifers.

As used herein, "first estrus cycle" refers to the estrus cycle after insemination. In cows the first estrus cycle is about 21 days following a previous estrus.

As used herein, "estrus" refers to the period during which an animal is most likely to become pregnant.

As used herein, "in heat" refers to being in the time of estrus, when an animal is most sexually receptive. In cows this period lasts about 12-18 hours.

As used herein, "behavioral estrus" refers to the behavioral demonstration that an animal is in heat, including showing standing heat.

As used herein, "standing heat" refers to the period during which a cow is receptive to a bull and will stand to be bred or stand to be mounted by other cows.

As used herein, "Day 0" is the day that an animal is in behavioral estrus or the day of breeding.

As used herein, "forcing estrus" refers to methods known in the art for forcing heat. Forcing estrus can include waiting periods, as appropriate.

As used herein, "forcing ovulation" refers to inducing ovulation, generally within one day of the treatment used to induce ovulation.

As used herein, "open" refers to an animal that is not pregnant.

As used herein, "cycling" refers to an animal that is experiencing an estrus cycle, i.e., is not pregnant.

As used herein, "readiness for breeding" refers to a time in the estrus cycle when breeding is most likely to result in pregnancy.

As used herein, "breeding" refers to methods known in the art that pertain to making a female animal pregnant. Such methods include natural and artificial insemination. Breeding methods may include a waiting time after observation of behavioral estrus or after forcing estrus. In cattle, the waiting time after observing behavioral estrus is 12-18 hours. In cattle, after forcing estrus with prostaglandin on Day 17, the waiting time is 72-80 hours. After the last hormone injection used in forcing ovulation, breeding should within about 24 hours, e.g., between about 0 to about 24 hours, and preferably about 16 hours after that injection, so that breeding will be done before ovulation occurs.

As used herein, "antibody specific to" refers to antibody that does not bind significantly to any sample components other than the desired component.

As used herein, "pregnancy testing" refers to testing for pregnancy and/or non-pregnancy.

As used herein, "whole blood" refers to blood as drawn. Whole blood contains a substantial amount of cells.

As used herein, "plasma" refers to blood with no substantial amount of cells. Plasma does contain clotting factors.

As used herein, "serum" refers to blood without a substantial amount of cells or clotting factors.

As used herein, "estrus synchronization" refers to a process whereby estrus for a group of animals is forced, such that each animal is likely to be in estrus within about a 2-5-day window.

As used herein "ovulation synchronization" refers to a process whereby ovulation for a group of animals is forced, such that each animal is likely to ovulate within a 3-4-day window.

As used herein, "estrus presynchronization" or "ovulation presynchronization" refers to a process whereby the estrus cycle, often for a group of animals, is blocked or forced into a particular stage of the cycle, so that estrus or ovulation synchronization procedures that are to be performed afterwards are more successful.

As used herein, "cowside" refers to an environment in which a domesticated animal is found, particularly in contrast to a laboratory environment.

As used herein, "breeding cycle time" refers to the time between one breeding of an animal and the next breeding during the next estrus cycle of the same animal.

As used herein, "pregnant mammal" refers to a mammal that has been inseminated and may be pregnant or to a plurality of inseminated mammals, some of which are likely to be pregnant.

As used herein, "maintaining pregnancy" refers to increasing the likelihood that an animal which has been inseminated will test positive for pregnancy of will deliver a live calf or increasing likelihood that a plurality of animals that have been inseminated will test positive for pregnancy or will deliver a live calf.

As used herein, "effective amount" refers to an amount of that is effective to produce the desired outcome.

As used herein, "administering" refers to any method of administering known in the art that produces that desired outcome. Examples of administering include but are not limited to injecting subcutaneously, intramuscularly and intravenously.

As used herein, "about 98% pure" refers to purity as measured by any method known in the art, including but not limited to protein electrophoresis.

As used herein, "insemination" refers to introducing semen by any method known in the art, including, but not limited to, natural and artificial insemination.

As used herein, "increasing likelihood of conception" refers to increasing the likelihood of detectable conception. For example, conception can be detected in bovines as early as about Day 15 after insemination by the presence of interferon-tau induced proteins.

As used herein, "decreasing the likelihood of embryo loss" refers to decreasing the chance that an inseminated mammal will test negative for pregnancy. As used herein, "decreasing the percentage of embryonic loss" with respect to a plurality of mammals that have been inseminated refers to decreasing the percentage of such animals that will test negative for pregnancy.

Baculovirus expression systems are well known in the art (O'Reilly et al. (1994) *Baculovirus Expression Vectors: A Laboratory Manual*, Oxford University Press).

There are many advantages to using baculovirus for heterologous gene expression. Heterologous cDNA is expressed well. Proper transcriptional processing of genes with introns occurs but expression is less efficient. As with other eukaryotic expression systems, baculovirus expression of heterologous genes permits folding, post-translational modification and oligomerization in manners that are often identical to those that occur in mammalian cells. The insect cytoplasmic environment allows proper folding and S—S bond formation, unlike the reducing environment of the *E. coli* cytoplasm. Post-translational processing identical to that of mammalian cells has been reported for many proteins. These include proper proteolysis, N- and O-glycosylation, acylation, amidation, carboxymethylation, phosphorylation, and prenylation. Proteins may be secreted from cells or targeted to different subcellular locations. Single polypeptide, dimeric and trimeric proteins have been expressed in baculoviruses. Finally, expression of heterologous proteins is under the control of the strong polyhedron promoter, allowing levels of expression of up to 30% of the total cell protein.

SF-9, SF-21, and High-Five insect cells are commonly used for baculovirus expression. SF-9 and SF-21 are ovarian cell lines from *Spodoptera frugiperda*. They are grown in Grace's (or a similar) media supplemented with 10% fetal calf serum, lactalbumin, and yeastolate. High-Five cells are egg cells from *Trichoplusia ni*. These cells are less expensive to maintain since they may be grown without fetal calf serum. They reportedly express higher levels of recombinant proteins, although we have found these differences to be minimal. All three cell lines may be grown at room temperature (optimum=25-27° C.), and do not require $CO_2$ incubators. Their doubling time is 18-24 hours. Expressed proteins can be recovered using protein purification methods known in the art, including use of fusion protein technology, immunoaffinity chromatography, and size-exclusion chromatography.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989 *Molecular Cloning*, Second Edition, cold Spring Harbor Laboratory, Plainview, N.Y.; Ausubel et al. (Eds.) (1995) *Current Protocols in Molecular Biology*, Greene Publishing and Wiley Interscience, New York; and Metzger et al. (1988) *Nature,* 334: 31-36. Many useful vectors for expression in bacteria, yeast, fungal, mammalian, insect, plant or other cells are well known in the art and may be obtained such vendors as Stratagene, New England Biolabs, Promega Biotech, and others. In addition, the construct may be joined to an amplifiable gene (e.g., the dihydrofolate reductase DHFR gene) so that multiple copies of the gene may be made. For appropriate enhancer and other expression control sequences, see also *Enhancers and Eukaryotic Gene Expression*, Cold Spring Harbor Press, NY (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art which is appropriate for the particular type of cell, including without limitation, transformation, lipofection or electroporation.

Additionally, it will be recognized by those skilled in the art that allelic variations may occur in the DNA sequences, which will not significantly change activity of the amino acid sequences of the peptides that the DNA sequences encode. All such equivalent DNA sequences are included within the scope of this invention Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

This invention provides methods and kits for maintaining pregnancy in mammals. Pregnancy is maintained by administration of effective amounts of luteinizing hormone (LH) or chorionic gonadotropin (CG). Both LH and CG may be used alone, in combination with each other, or in combination with growth hormone (GH) or follicle stimulating hormone (FSH). Hormones are preferably administered on about Day 4 to about Day 7 following insemination. Effective amounts of LH range from about 25 micrograms to about 25 milligrams and of CG range from about 100 IU (international units) to about 2000 IU. Mammals treatable by the methods of this invention include ungulates and related mammals, including bovines. Kits provided by this invention include effective amounts of one or more hormones, a device for administering the hormone(s) and instructions.

In the practice of this invention, hormone compositions of this invention are administered to mammals that are possibly pregnant as a result of insemination. Insemination is performed by any method known in the art, including artificial insemination. Preferably insemination is performed by timed artificial insemination after synchronization of ovulation. Ovulation synchronization optionally includes ovulation presynchronization, and is preferably performed by the methods of this invention.

In the practice of this invention, luteinizing hormone is administered to one or more pregnant mammals to maintain pregnancy. A pregnant mammal may be a mammal that is possibly pregnant from having been inseminated, preferably during estrus, which may not even be detectably pregnant, and a plurality of pregnant mammals may be a plurality of mammals only some of which are pregnant.

In one embodiment of this invention, LH is recombinant LH. The LH may be produced in a baculovirus or mammalian or other expression system. In one embodiment, recombinant LH is recovered from the milk or egg whites of a transgenic animal. Methods of producing recombinant proteins in transgenic animals are well known and have been described in U.S. Pat. Nos. 4,873,316, 5,322,775, 6,111,165, 6,472,584 and 6,528,699 and other means known in the art.

In another embodiment, LH is purified from pituitary cells or pituitary tissue. Bovine LH can be purified by methods known in the art, and purified bovine LH is available on the market (AspenBio Inc., Castle Rock, Colo., Scripps Laboratories, San Diego, Calif. and BioTrend, Cologne, Germany). Purified bovine LH is also available from the NIH National Hormone and Pituitary Program (NHPP, Torrance, Calif.). When recombinant LH is used in the practice of this invention, the recombinant LH is similar structurally and has activity similar to native, purified LH. Recombinant LH can be made using cloned and mutated LH genes that encode peptides identical to native LH, or having at least about 80% homology thereto, more preferably having at least about 90% homology thereto, and most preferably having at least about 95% homology thereto and also being able to induce ovulation in a mammal. Recombinant LH made can also be made using cloned and mutated LH genes that encode peptides that are not identical to native LH, of the selected species, providing that the recombinant LH produced has a similar activity as native LH.

Recombinant LH can also be made in accordance with the methods known to the art, e.g., as described in US Patent Application Publication No. 20030059898 assigned to Genzyme by Beck et al., and U.S. Pat. Nos. 6,635,256, 6,242,580, 6,238,890, 6,225,449, 6,103,501, 6,028,177, 5,985,611, 5,958,737, 5,883,073, 5,792,460, 5,759,818, 5,733,735, 5,712,122, 5,705,478, 5,585,345, 5,405,945, 5,338,835 and 5,177,193, and U.S. Patent Publication Numbers 20020160944, and 20010007757, and other means known to the art.

In the practice of this invention, chorionic gonadotropin hormone is from primates, including humans, and horses. Hormones from the species to be treated, as well as hormones from other species are useful in the practice of this invention. Use of hormones from the species to be treated is less likely to cause an immune response in the treated mammal.

In an embodiment of this invention, growth hormone is bovine somatotrophin (bST). In an embodiment of this invention, FSH is human FSH or bovine FSH.

In the practice of this invention, pregnancy is tested by any pregnancy test known in the art, including by ultrasound or by testing for pregnancy-indicating molecules, at times appropriate for the selected species, as is known in the art. When the treated animal is a bovine, pregnancy can be tested by testing for the presence of interferon-tau induced proteins at about Day 15 (U.S. Patent Application Nos. 60/377,987; 60/377,166; 60/380,043; 60/377,921; 60/377,165; 60/377,355; 60/377,829; and 60/380,042), and/or by ultrasound at about Days 28, 45, or 56.

In the practice of this invention, if a mammal is determined to not be pregnant after practicing the methods of this invention, the next cycle of estrus can be forced by methods known in the art.

The methods of this invention are useful in mammals that are in estrus for the first time, have been in estrus more than once, have never had offspring, have had one or more offspring, have never been administered a hormone composition of this invention for maintaining pregnancy, or have been previously administered a hormone composition of this invention for maintaining pregnancy. The methods of this invention are specifically useful on mammals that have previously been administered hormone compositions of this invention for the purpose of maintaining pregnancy.

In an embodiment of this invention, bovine LH is administered to a pregnant bovine, or a plurality of pregnant bovines, on about Day 4 to about Day 7 after insemination. In an embodiment of this invention, bovine LH is administered to a pregnant bovine, or a plurality of pregnant bovines, on about Day 4 to about Day 5 after insemination. In an embodiment of this invention, bovine LH is administered to a pregnant bovine, or a plurality of pregnant bovines, on about Day 2 to about Day 10 after insemination.

In an embodiment of this invention, pregnant mammals may be screened by ultrasound for the presence of a sufficiently mature follicle before administration of a hormone composition of this invention. In an embodiment of this invention, a mature follicle of a bovine is at least about 10 mm in diameter. In an embodiment of this invention, after administration of LH, ultrasound is performed on the mammal to screen for ovulation and luteinization, (corpus luteum production).

In an embodiment of this invention, bovine LH is administered in an amount ranging from about 10 micrograms to about 25 milligrams, from about 25 micrograms to about 5 milligrams, from about 25 micrograms to about 1 milligram, from about 25 micrograms to about 250 micrograms, from about 25 micrograms to about 175 micrograms, or from about 25 micrograms to about 100 micrograms, or from about 25 micrograms to about 75 micrograms. An average cow weighs about 1,000 to about 1,500 pounds. In an embodiment of this invention, bovine LH is administered in an amount that equates to about 10 nanograms to about 25 micrograms per pound of cow.

In an embodiment of this invention, human CG is administered in an amount ranging from about 100 IU to about 2000 IU, from about 100 IU to about 1750 IU, or from about 250 IU to about 1000 IU.

In an embodiment of this invention, the hormone composition that is to be administered is about 90% pure, about 95% pure, about 98% pure, about 99% pure, or about 100% pure, as determined by a protein purification assay known in the art.

Mammals treatable by the methods of this invention include ungulates and related mammals. Mammals treatable by the methods of this invention include, but are not limited to cattle, sheep, goats, yaks, water buffaloes, bison, antelopes, gazelles, elk, reindeer, moose, bighorn sheep, giraffes, and camelids including bactrian and dromedary camels, llamas, swine, horses, alpacas, and vicunas.

Preferably a hormone composition of this invention is derived from the same species as the species of mammal to be administered with said composition. If the mammal is cattle, preferably the hormone composition to be administered in the practice of this invention comprises one or more hormones that are all derived from cattle or from cattle genes.

In an embodiment of this invention, a hormone composition to be administered also contains other components useful for injection as known in the art. Other components useful for injection include, but are not limited to, adjuvant and saline.

In an embodiment of this invention, a hormone composition of this invention is administered more than once after insemination. In an embodiment of this invention, more than one hormone composition of this invention is administered.

In the practice of this invention, pregnancy is maintained in at least about forty percent, at least about forty-two percent, at least about forty-five percent, at least about fifty percent, at least about fifty-five percent, or at least about sixty percent of cows treated using the compositions and methods of this invention.

Although applicant does not wish to be bound by a particular theory, administration after insemination of hCG and/or bLH may act by inducing accessory corpus luteum formation which increases the secretion of progesterone and increases serum progesterone concentrations during the critical time when the uterus must recognize the pregnancy, resulting in increased maintenance of pregnancies.

Untreated follicular cysts in an open animal can prevent an animal from cycling normally. This invention also provides a method useful in the treatment of follicular cysts in mammals, most preferably, cows. At least about 2 mg up to about 10 mg of luteinizing hormone should be injected (preferably intramuscularly) into a cow in which a follicular cyst has been diagnosed. Those of skill in the art are able to optimize dosages based on animal size, and the teachings hereof without undue experimentation. Successful resolution of the cyst may be confirmed by ultrasound or other means known to the art. If the animal is pregnant and has a normal corpus luteum in the presence of the cyst, treatment is generally not necessary.

This invention also provides methods for synchronizing ovulation in a plurality of female animals. A number of techniques are known for synchronizing estrus, many of which call for the use of gonadotropin releasing hormone (GnRH), a hormone which is secreted from the hypothalamus and affects the anterior pituitary. This invention involves substituting GNRH with luteinizing hormone. The LH provides more effective synchronization than GNRH. The LH is administered in effective amounts, preferably in amounts between about 2 mg and about 10 mg in cattle. One skilled in the art can optimize dosages based on animal size and response without undue experimentation.

One estrus synchronization system known to the art is the MGA/GnRH/PGF$_2$ System (Wood, S. L., et al. (2001), "Improved synchrony of estrus and ovulation with the addition of GNRH to a melengestrol acetate-prostaglandin synchronization treatment in beef heifers," J. Anim. Sci. 79:2210-2216). Melengestrol acetate (MGA) is an orally active synthetic progestin that was developed to control estrus in feedlot heifers (Lauderdale, et al., 1977). This progestin can be used in estrous synchronization to mimic progesterone and can stimulate estrus in heifers. Since small amounts of MGA are used, be careful when mixing bulk rations to ensure even distribution throughout the ration. PGF$_2$ is prostaglandin, a hormone released from the uterus once the female recognizes she is not pregnant. Prostaglandin causes the CL to regress or diminish and, once this occurs, progesterone concentrations decrease rapidly.

The MGA/GnRH/PGF$_2$ system includes the following steps: Feed MGA for 14 days at 0.5 mg/hd/d. On day 26, inject a shot of GNRH IM; follow this 7 days later (day 33) by a shot of prostaglandin IM. Heat check and breed from day 33 to day 38 (see FIG. 1).

In the system of this invention, used for ovulation synchronization, LH in the above-described dosage is administered instead of GNRH. If desired, the animal can be bred immediately after this treatment. In this invention, progestin may be substituted for MGA. MGA is illegal for use in lactating dairy cows, but the method is useful for beef producers.

Figure 2:
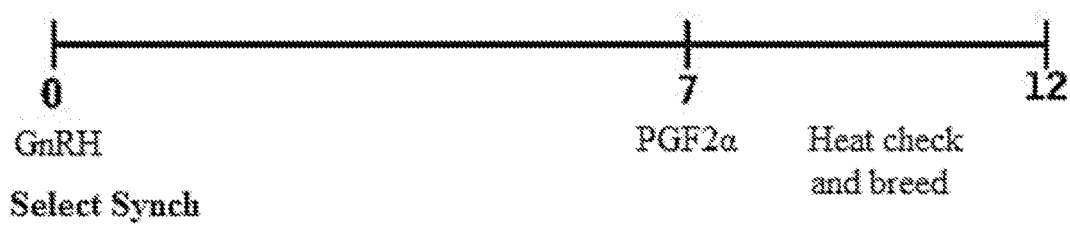
FIG. 2 illustrates a timeline for a "Select Synch" intramuscular GnRH injection estrus synchronization system.

Other estrus synchronization systems known to the art include the Select Synch system. This system comprises the following steps: Inject GNRH intramuscularly (IM) on day 0, followed by prostaglandin IM on day 7. Research by Geary and Whittier (Geary, T. W., and J. C. Whittier (1999), "Various protocols for synchronization of estrus or ovulation using GNRH and prostaglandin," 1999 Beef Program Report. Department of Anim. Sci., Colorado State University) report pregnancy rates of 61 percent for cattle bred based on standing heat (see FIG. 2).

Figure 3:
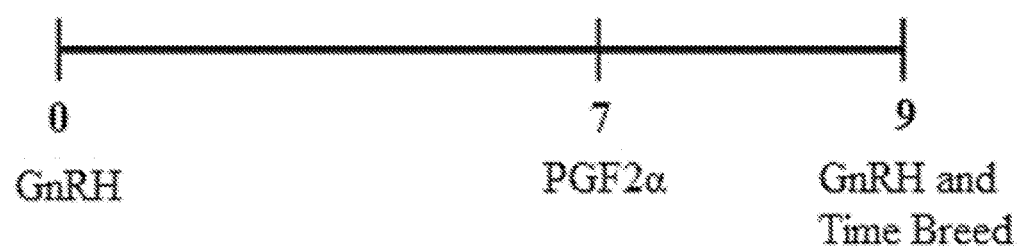
FIG. 3 illustrates a timeline for a "Co-Synch" estrus or ovulation synchronization system.

Another estrus synchronization method is the Co-Synch system (Geary, T. W., and J. C. Whittier (1999), "Various protocols for synchronization of estrus or ovulation using GNRH and prostaglandin," 1999 Beef Program Report. Department of Anim. Sci., Colorado State University), which involves the following steps: Inject GNRH IM on day 0, followed by prostaglandin IM on day 7. Inject GNRH again on day 9; then time breed (see FIG. 3).

Figure 4:
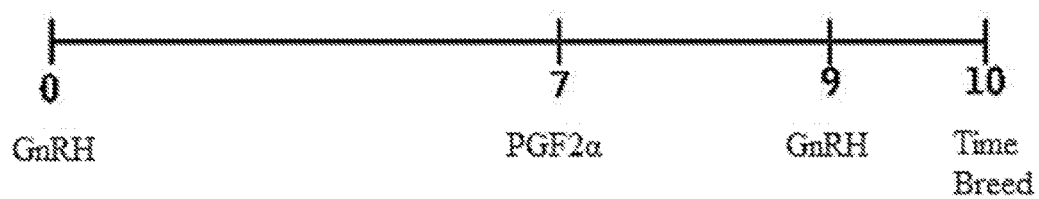
FIG. 4 illustrates a timeline for a "Ov-Synch" estrus synchronization system.

A further estrus synchronization system is the Ov-Synch system (Geary, T. W., and J. C. Whittier (1999), "Various protocols for synchronization of estrus or ovulation using GnRH and prostaglandin," 1999 Beef Program Report. Department of Anim. Sci., Colorado State University), which involves the following steps: Inject GnRH IM on day 0, followed by prostaglandin IM on day 7. Inject GNRH again at day 9, and time breed on day 10 (see FIG. 4).

Another common estrus synchronization program in dairy cattle is called Heatsynch which uses GNRH (day 0), PGF (day 7), then estradiol cipronate (ECP) (day 8). Cows are observed for heat and bred at any heat. Any cows that are not found in heat are time bred 48 hours after the ECP injection (day 10).

In the systems of this invention, LH is substituted for GNRH in the dosages described above.

The following examples are provided for illustrative purposes, and are not intended to limit the scope of the invention as claimed herein. Any variations in the exemplified articles that occur to the skilled artisan are intended to fall within the scope of the present invention.

EXAMPLES

Example 1

Expression of Recombinant bLH in a Baculovirus Expression System

DNA sequences encoding the alpha and beta bovine luteinizing hormone subunits are ligated into a bacterial transfer vector. Inserts for protein purification are optionally included. The insert is flanked by portions of viral genes to permit homologous recombination with replication defective, linear, viral DNA. The direction of the inserts relative to the polyhedron promoter is verified. The sequences of the inserts are optionally verified. Plasmids are purified for transfection into insect cells.

Insect cells are cotransfected with the alpha and beta LH recombinant transfer vectors and linearized viral vector. Optionally, alpha and beta LH transfections are performed individually. Transfection and transformation methods are well known in the art and include electroporation, lipid, and calcium phosphate-mediated transformation methods. Replicative viruses form by intracellular homologous recombination between the ends of the viral molecules and portions of the transfer vector flanking alpha and beta LH. Alpha and beta bovine LH are inserted into the virus and complement defective viral gene(s) to permit viral replication. Marker proteins are optionally included and expressed upon selected insertion events.

The transfected cell supernatants are harvested. Insect cells are infected with dilutions of the supernatant to isolate single virus plaques that optionally express marker proteins. Additional insect cells are infected with virus from selected plaques to amplify the quantity and titer of viral stocks. Protein expression is optionally examined by Western blotting. Protein expression and activity is tested by bioassay.

Example 2

Estrus Synchronization and Artificial Insemination Control

Several hundred cows were induced to ovulate using a standard estrus synchronization protocol, artificially inseminated, and intravenously administered sterile water.

On Days 14 and 21 serum was collected for progesterone assay. These collection times represent the critical period for progesterone to maintain pregnancy, and the expected time of lowest progesterone concentration if the animal is not pregnant and returns to estrus. Ultrasound examination of the ovarian structures was performed on Days 14 and 21 to evaluate correlation of CL size and progesterone concentration, and to allow comparison of both measurements with treatment and with outcome of the breeding. On post insemination Days 28, 35, and 56, ultrasound examination of the uterus was used to determine pregnancy status. Day 28 is the earliest time for reliably visualizing a pregnancy. Pregnancies were closely monitored at these times to determine rates of embryonic loss and final outcome of each breeding.

Data was analyzed by statistical software (SAS). Herd and season effects were analyzed using ANOVA and regression analysis. At Day 56, 38% of treated cows were pregnant.

Example 3

Administration of 1660 IU hCG on Day 7 After Insemination

On a weekly basis, cows at the end of the elective waiting period were induced to ovulate using a standard estrus synchronization protocol, and at the time of breeding each cow was assigned to either the treatment or control group (Example 2) on an alternating basis. On Day 7, post-breeding cows were intramuscularly administered 1,660 IU hCG. (The World Health Organization standard for hCG activity has been determined to be approximately 10,000 IU per milligram.)

On Days 14 and 21 serum was collected for progesterone assay. These collection times represent the critical period for progesterone to maintain pregnancy, and the expected time of lowest progesterone concentration if the animal is not pregnant and returns to estrus. Ultrasound examination of the ovarian structures was performed on Days 14 and 21 to evaluate correlation of CL size and progesterone concentration, and to allow comparison of both measurements with treatment and with outcome of the breeding. On post insemination Days 28, 35, and 56, ultrasound examination of the uterus was used to determine pregnancy status. Day 28 is the earliest time for reliably visualizing a pregnancy. Pregnancies were closely monitored at these times to determine rates of embryonic loss and final outcome of each breeding.

Several hundred cows were tested. Data was analyzed by statistical software (SAS). Herd and season effects were analyzed using ANOVA and regression analysis. At Day 56, 50% of treated cows were pregnant.

Example 4

Administration of 830 IU hCG on Day 7 After Insemination

Several hundred cows at the end of the elective waiting period were induced to ovulate using a standard estrus synchronization protocol, and at the time of breeding each cow was assigned to either the treatment or control group (Example 2) on an alternating basis. On Day 7, post-breeding cows were intramuscularly administered 1,660 IU hCG.

On Days 14 and 21 serum was collected for progesterone assay. Ultrasound examination of the ovarian structures was performed on Days 14 and 21 to evaluate correlation of CL size and progesterone concentration, and to allow comparison of both measurements with treatment and with outcome of the breeding. On post insemination Days 28, 35, and 56, ultrasound examination of the uterus was used to determine pregnancy status. Pregnancies were closely monitored at these times to determine rates of embryonic loss and final outcome of each breeding.

Several hundred cows were tested. Data was analyzed by statistical software (SAS). Herd and season effects were analyzed using ANOVA and regression analysis. At Day 56, 52% of treated cows were pregnant.

Example 5

Administration of 830 IU hCG on Day 5 After Insemination

Cows are forced into estrus, artificially inseminated, and intramuscularly administered 830 IU hCG on Day 5 after insemination. Serum is collected on Days 14 and 21 and assayed for progesterone. Ultrasound is performed on Days 14 and 21. Ultrasound examination is performed on Days 28, 35, and 56. At Day 56, at least about 50% of cows are pregnant.

Example 6

Administration of 156, 83, 25 and 10 Micrograms and 1, 10 and 25 mg bLH on Day 5 After Insemination Cows are forced into estrus, artificially inseminated, and intramuscularly administered 156, 83, 25 and 10 micrograms or 1, 10 and 25 mg bLH, purified from bovine pituitary, on Day 5 after insemination. Serum is collected on Days 14 and 21 and assayed for progesterone. Ultrasound is performed on Days 14 and 21. Ultrasound examination is performed on Days 28, 35, and 56. At Day 56, improvement in maintenance of pregnancy is shown compared to cows not administered bLH or other hormone, and cows administered hCG only.

Example 7

Administration of 156, 83, 25 and 10 Micrograms and 1, 10 and 25 mg bLH on Day 5 After Insemination Cows are forced into estrus, artificially inseminated, and intramuscularly administered 156, 83, 25 and 10 micrograms or 1, 10 and 25 mg recombinant bLH, obtained from a baculovirus expression system (Example 1), on Day 5 after insemination. Serum is collected on Days 14 and 21 and assayed for progesterone. Ultrasound is performed on Days 14 and 21. Ultrasound examination is performed on Days 28, 35, and 56. At Day 56, improvement in maintenance of pregnancy is shown compared to cows not administered bLH or other hormone, and cows administered hCG only.

Example 8

Intravenous Administration of 10 Micrograms bLH on Day 5 After Insemination

Cows are forced into estrus, artificially inseminated, and intravenously administered 10 micrograms bLH, purified from bovine pituitary, on Day 5 after insemination. Serum is collected on Days 14 and 21 and assayed for progesterone. Ultrasound is performed on Days 14 and 21. Ultrasound examination is performed on Days 28, 35, and 56. At Day 56, improvement in maintenance of pregnancy is shown compared to cows not administered bLH or other hormone, and cows administered hCG only.

Example 9

Development of Accessory Corpus Lutea

Tests were performed over a three-month period utilizing a total of 31 cows in eight different tests. Bovine luteinizing hormone was administered in varying dosage levels, from 0.5 mg to 8 mg in sterile saline to cows four days after artificial insemination. Tests determined that an effective dosage level was 2 mg, intravenously, or greater. Using this 2 mg dosage in a limited trial of 15 cows, we were able to create at least one accessory corpus luteum in twelve cows (80% response). Ovaries were examined by ultrasound both before and after treatment using a Sonosite VET180plus with an 11 mm broadband sector transducer with a range of 4-7 mHz. The after-treatment scan was performed seven days after injection. Results are shown in Table 1.

TABLE 1

PRODUCTION OF ACCESSORY CORPUS LUTEUM BY INJECTION OF BOVINE LUTEINIZING HORMONE

| Dose (mg) | Number Responding* | Number Treated | Percent Responding |
|---|---|---|---|
| 0.5 | 0 | 1 | 0 |
| 1 | 0 | 3 | 0 |
| 2 | 12 | 15 | 80 |
| 3 | 5 | 5 | 100 |
| 4 | 3 | 3 | 100 |
| 6 | 2 | 2 | 100 |
| 7 | 1 | 1 | 100 |
| 8 | 1 | 1 | 100 |

*Response = development of at least one accessory corpus luteum.

This response is comparable to the accessory corpus luteum formation found after administering a dose of human chorionic gonadotropin (hCG) to lactating dairy cattle.

Example 10

Treatment of Follicular Cysts in Cattle

Three non-pregnant, non-inseminated cows were examined by ultrasound to determine the presence of follicular cysts. The cows were treated with injections of 2 mg luteinizing hormone in saline. Seven more non-pregnant, non-inseminated cows diagnosed with follicular cysts were treated as above. Forty-eight hours after treatment, the cows are examined for the presence of cysts using ultrasound to confirm that the cysts have resolved.

Example 11

Ovulation Synchronization

Ten non-pregnant cows not exhibiting signs of being in heat are injected with 2 mg luteinizing hormone, IM. Seven days later, the cows are injected IM with 25 mg prostaglandin. 9 days later, the cows are again injected with 2 mg of luteinizing hormone. The cows are artificially inseminated within a few hours after the second injection of luteinizing hormone, resulting in a pregnancy rate greater than about forty percent. Compared with the use of GnRH, the use of LH provides more reliable synchronization and a greater pregnancy rate.

Example 12

Cloning of bLH Alpha Subunit

RNA was extracted from 1 bovine pituitary gland using RNeasy Midiprep (Qiagen cat#75142). RT-PCR was performed using Superscript One-Step RT PCR with Platinum Taq (Invitrogen cat#10928-034). Primers used in this reaction were bLH alpha BamH1 U (GGATCCATGGGATTAC-TACAGAAA) and bLH alpha RI L (GAATTCTTAG-GATTTGTGATAATAAC). RT-PCR product was gel purified using QiaQuick (Qiagen cat#28704). Purified product was polished and ligated into pCRScript cloning vector using kit reagents (Statagene cat#211188). Ligation was transformed into Top 10 electro competent *E. Coli* (Invitrogen cat#C4040-50) and plated onto LB agar with ampicillin. Transformants were analyzed by restriction digest using BamHI (NEB cat# R0136S) and sequence confirmed by DNA sequencing (MMR).

Example 13

Cloning of bLH Beta Subunit

RNA was extracted from 3 bovine pituitary glands using Tri-Reagent BD (Sigma cat# T3809). DNA was synthesized using iScript cDNA Synthesis Kit (BioRad cat#170-8890). Primary PCR was performed using the above cDNA, Deep Vent DNA Polymerase (NEB cat# M0258S) and the following primers: bLH-B L 9-9-0 (TTTCCAGAGTTAG-GATGGGCATGG) and bLH-B U 9-9-03 (CAAGGATG-GAGATGTTCCAGGGAC). Secondary PCR was performed using the primary PCR product as template, Deep Vent DNA Polymerase and the following primers: 5'bglME-bLHb (AGATCTATGGAGATGTTCCAGGGACTG) and 3'bLHbetaR1 (GAATTCAGTGGGGCATCCTTAGAG-GAAGAG). Secondary PCR product was gel purified using QiaQuick and adenosine extension reaction was performed using PCR Master Mix (Promega cat# M7501). The product was ligated into pCR2.1 TOPO Cloning Vector (Invitrogen cat# K4500-01). Ligation was transformed into chemical competent Top 10F' *E. coli* (Invitrogen cat# C3030-03) and plated onto LB agar with ampicillin. Transformants were analyzed by restriction digest using EcoRI (NEB cat# R0101S) and sequence confirmed by DNA sequencing (Lark Technologies).

Example 14

Insect Expression Strategies
Baculovirus Expression

Bovine LH alpha and beta are inserted into pBac4x-1 (Novagen cat#70045-3) separately and together for both individual and dual expression using the BacVector (Novagen cat#70077) Baculovirus Expression system in sf9, Sf21, and High Five insect cells. Bovine LH alpha and beta are inserted into pFastBack Dual (Invitrogen cat#10712-024) for dual expression in Sf9, Sf21, and High Five insect cells.

Bovine LH Alpha Into pBac4x-1 bLH alpha in pCRScript and pBac4X-1 were digested with NotI (NEB cat# R0189S) and XhoI (NEB cat# R0146S). bLH alpha insert and cut vector were gel purified using QiaQuick and ligated using T4 DNA Ligase (NEB cat# M0202S). Ligation was transformed into electro competent Top10 E. coli and plated onto LB agar with ampicillin. Transformants were analyzed by restriction digest using NotI and XhoI and sequence was confirmed by DNA sequencing (Lark Technologies).

Bovine LH beta into pBac4x-1 bLH beta in pCR2.1 and pBac4x-1 were digested with Bgl II (NEB cat# R0144S) and EcoRI. bLH beta insert and cut vector were gel purified using QiaQuick and ligated using T4 DNA Ligase (NEB). Ligation was transformed into electro competent XLI Blue and plated onto LB agar with ampicillin. Transformants were analyzed by restriction digest using Bgl II and EcoRI and sequence was confirmed by DNA sequencing (Lark Technologies).

Bovine LH Alpha and Beta Into pBac4x-1 bLH alpha and bLH beta each in pBac4x-1 were cut with AgeI (NEB cat# R0552S) and Bgl II. The fragment containing the alpha insert and the fragment containing the beta subunit were gel purified using QIAex II (Qiagen cat#20021). Fragments were ligated together using T4 DNA Ligase (NEB). Ligation was transformed into chemical competent Top10 E. coli and plated onto LB agar with ampicillin. Transformants were analyzed by restriction digest using EcoRI and sequence confirmed by DNA sequencing (Lark Technologies).

Insect Cell Line Expression

Bovine LH alpha and beta are inserted into pIZ/V5-His (Invitrogen cat# V8000-01) and pIB/V5-His (Invitrogen cat# V8020-01) separately for co-expression using the InsectSelect System for stable cell line expression in Sf9, Sf21 and High Five insect cells. Co-expression is performed using bLH alpha/pIZ/V5-His with bLH beta/pIB/V5-His and also using bLH alpha/pIB/V5-His with bLH beta/pIZ/V5-His. Stable lines expressing single chains are also be infected with baculovirus encoding the complementary chain.

Bovine LH Alpha Into pIZ/V5-His bLH alpha in pBac4X-1 and pIZ/V5-His were each digested with BamHI and EcoRI. Fragments containing bLH alpha and cut pIZ/V5-His were gel purified using QIAex II. Fragments were ligated together using T4 DNA Ligase (Invitrogen cat#15224-017). Ligation was transformed into electro competent Top10 E. coli (Invitrogen cat# C664-11) and plated onto LB agar with Zeocin. Transformants were analyzed by restriction digest with Sac (NEB cat# R0156) and EcoRI and sequence confirmed by DNA sequencing (lark Technologies).

Bovine LH Beta Into pIZ/V5-His bLH beta in pCR2.1 was digested with Bgl II and EcoRI and pIZ/V5-His was digested with BamHI and EcoRI. Fragments containing bLH beta and cut pIZ/V5-His were gel purified using QIAex II. Fragments were ligated together using T4 DNA Ligase (Invitrogen). Ligation was transformed into electro competent Top10 E. coli and plated onto LB agar with Zeocin. Transformants were analyzed by restriction digest with Sac1 and EcoRI and sequence confirmed by DNA sequencing (Lark Technologies)

Bovine LH Alpha Into pIB/V5-His and Bovine LH Beta Into pIB/V5-His

The cloning strategy follows pIZ/V5-His with the exception that clone selection occurs using ampicillin and cell selection occurs using blasticidin.

Example 15

Mammalian Expression Strategies

Bovine LH alpha and beta is inserted into pBudCE4.1 (Invitrogen cat# V532-20) for dual expression in COS7, CHO, 293 and 3T3 mammalian cells. Bovine LH alpha and beta are also inserted into pBudCE4.1 and pWE1 (ATCC cat#87 678) separately for co-expression in COS7, CHO, 293 and 3T3 mammalian cells. Co-expression is performed using bLH alpha/pBudCE4.1 with bLH beta/pWE1 and also using bLH alpha/pWE1 with bLH beta/pBudCE4.1.

Bovine LH alpha and beta subunits into pBudCE4.1 (Invitrogen cat# V532-20) for dual expression in COS7, CHO, 293 and 3T3 mammalian cells is as follows: bLH alpha is inserted into pBudCE4.1 using the NotI/XhoI sites. bLH beta is inserted into pBudCE4.1 using the BamH1/EcoR1 sites. Bovine LH alpha and beta is inserted into pWE1 using BamH1 and EcoR1.

Example 16

Single-Chain Recombinant Bovine LH

Single-chain recombinant bovine LH can be made in accordance with the methods described in U.S. Pat. No. 6,242,580, which discloses recombinant LH wherein the beta subunit is covalently linked to the alpha subunit. Alternatively, a linker is present between the beta and alpha subunits. Single-chain forms need only a single gene to be transcribed during recombinant production and are advantageous over the dimeric forms in terms of stability of the protein. SEQ ID NOs 1-4 present the nucleotide sequences for bovine LH beta and alpha subunits. Expression vectors where the C-terminus of the bovine beta subunit is linked to the N-terminus of the bovine alpha subunit are transfected into CHO cells for expression.

It will be appreciated by those of ordinary skill in the art that methods, compositions, and kits other than those specifically disclosed herein are available in the art and can be employed in the practice of this invention. All art-known functional equivalents are intended to be encompassed within the scope of this invention.

```
SEQ ID NO:1
X00050. Bovine mRNA for a...[gi:606]
LOCUS    BTPASH      713 bp   mRNA    linear   MAM 30-MAR-1995
DEFINITION Bovine mRNA for alpha-subunit of pituitary hormones. (glycoprotein
           hormones).
ACCESSION X00050 J00009 K00527 V01493
```

-continued

```
VERSION     X00050.1  GI:606
KEYWORDS    glycoprotein; hormone; signal peptide.
SOURCE      Bos taurus (cow)
  ORGANISM  Bos taurus
            Eukaryota; Metazoa; Chordata; Craniata; Vertebrata; Euteleostomi;
            Mammalia; Eutheria; Cetartiodactyla; Ruminantia; Pecora; Bovoidea;
            Bovidae; Bovinae; Bos.
REFERENCE   1  (bases 98 to 661)
  AUTHORS   Nilson,J.H., Thomason,A.R., Cserbak,M.T., Moncman,C.L. and
            Woychik,R.P.
  TITLE     Nucleotide sequence of a cDNA for the common alpha subunit of the
            bovine pituitary glycoprotein hormones. Conservation of nucleotides
            in the 3'-untranslated region of bovine and human pre-alpha subunit
            mRNAs
  JOURNAL   J. Biol. Chem. 258 (8), 4679-4682 (1983)
  MEDLINE   83161058
   PUBMED   6187740
REFERENCE   2  (bases 1 to 713)
  AUTHORS   Erwin,C.R., Croyle,M.L., Donelson,J.E. and Maurer,R.A.
  TITLE     Nucleotide sequence of cloned complementary deoxyribonucleic acid
            for the alpha subunit of bovine pituitary glycoprotein hormones
  JOURNAL   Biochemistry 22 (20), 4856-4860 (1983)
  MEDLINE   84024633
   PUBMED   6688736
COMMENT     Data kindly reviewed (09-MAY-1985) by R.A. Maurer.
FEATURES             Location/Qualifiers
     source          1..713
                     /organism="Bos taurus"
                     /db_xref="taxon:9913"
     mRNA            <1..713
                     /product="messenger RNA"
     CDS             78..440
                     /note="alpha-subunit precursor"
                     /codon_start=1
                     /protein_id="CAA24932.1"
                     /db_xref="GI:607"
                     /db_xref="SWISS-PROT:P01217"

/translation="MDYYRKYAAVILTILSLFLQILHSFPDGEFTMQGCPECKLKENK

YFSKPDAAIYQCMGCCFSRAYPTPARSKKTMLVPKNITSEATCCVAKAFTKATVMG

NV

RVENHTECHCSTCYYHKS"
     sig_peptide     78..149
                     /note="signal peptide"
     mat_peptide     150..437
                     /product="alpha-subunit"
     misc_feature    688..693
                     /note="polyA signal"
     polyA_site      713
                     /note="polyadenylation site"
BASE COUNT            209 a    164 c    133 g    207 t
ORIGIN 1 aaaaactaaa attcttcttc agatccacag tcaactgccc tgactacatt ctgcaaaaat
   61 ccagaggacg aagagccatg gattactaca gaaaatatgc agctgtcatt ctgaccattt
  121 tgtctctgtt tctgcaaatt ctccattcct ttcctgatgg agagtttaca atgcagggct
  181 gtcctgaatg caagctaaaa gaaaacaaat acttctccaa gccagatgct gcaatctatc
  241 agtgcatggg gtgctgcttc tccagggcat accccactcc agcgaggtct aagaagacaa
  301 tgttggtccc caagaacatc acctcggaag ctacatgctg tgtggccaaa gcatttacca
  361 aggccacagt gatgggaaat gtcagagtgg agaaccacac cgagtgccac tgcagcactt
  421 gttattatca caaatcctaa tagtttgcag tgggccttgc tgatgatggc tgacttgctc
  481 aaaaggaaaa ttaatttgtc cagtgtctat ggctttgtga gataaaaccc tccttttcct
  541 tgccatacca ttttttaacct gctttgagaa tatactgcag ctttattgct tttctcctta
  601 tcctacaata taatcagtag tcttgatctt ttcatttgga atgaaatatg gcatttagca
  661 tgaccataaa aagctgattc cactggaaat aaagtctttt aaatcatcac tct
//
```

-continued

```
Revised: July 5, 2002.
SEQ ID NO:2
M10077. Bovine lutropin (...[gi:163300]
LOCUS       BOVLHBX        629 bp    mRNA    linear   MAM 27-APR-1993
DEFINITION  Bovine lutropin (LH) beta subunit mRNA, complete cds.
ACCESSION   M10077
VERSION     M10077.1  GI:163300
KEYWORDS    glycoprotein; lutropin.
SOURCE      Bos taurus (cow)
   ORGANISM Bos taurus
            Eukaryota; Metazoa; Chordata; Craniata; Vertebrata; Euteleostomi;
            Mammalia; Eutheria; Cetartiodactyla; Ruminantia; Pecora; Bovoidea;
            Bovidae; Bovinae; Bos.
REFERENCE   1  (bases 1 to 629)
   AUTHORS  Maurer,R.A.
   TITLE    Analysis of several bovine lutropin beta subunit cDNAs reveals
            heterogeneity in nucleotide sequence
   JOURNAL  J. Biol. Chem. 260 (8), 4684-4687 (1985)
   MEDLINE  85182575
   PUBMED   3838746
COMMENT     Original source text: Bovine pituitary lambda gt-11 library, cDNA
            to mRNA, clones LH[-7,-14,-8,-6].
            Variations between the four clone sequences most likely reflects
            different processing of the precursor mRNAs [1].
            Draft entry and sequence [1] in computer-readable form kindly
            provided by R. Maurer (04-OCT-1985).
   FEATURES       Location/Qualifiers
      source      1..629
                  /organism="Bos taurus"
                  /db_xref="taxon:9913"
      mRNA        <1..514
                  /note="LHb mRNA (clone LH-7)"
      CDS         2..421
                  /note="luteinizing hormone beta subunit prepeptide"
                  /codon_start=1
                  /protein_id="AAA30623.1"
                  /db_xref="GI:163301"

/translation="MFQGLLLWLLLGVAGVWASRGPLRPLCQPINATLAAEKEACPVC

ITFTTSICAGYCPSMKRVLPVILPPMPQRVCTYHELRFASVRLPGCPPGVDPMVSFPV

ALSCHCGSCRLSSTDCGGPRTQPLACDHPPLPDILFL"

sig_peptide 2..55
                  /note="luteinizing hormone beta subunit signal peptide"
      mat_peptide 56..418
                  /product="luteinizing hormone beta subunit"
      mRNA        <28..629
                  /note="LHb mRNA (clone LH-14)"
      mRNA        <31..514
                  /note="LHb mRNA (clone LH-8)"
      mRNA        <70..514
                  /note="LHb mRNA (clone LH-6)"
      variation   169
                  /note="c in clones LH[-7,-14,-8]; t in clone LH-6"
      variation   178..182
                  /note="gaagc in clones LH[-7,-14,-6]; gc in clone LH-8"
      variation   329
                  /note="t in clone LH-7; c in clones LH[-6,-8,-14]"
      variation   447
                  /note="c in clones LH[-7,-8,-6]; t in clone LH-14"
BASECOUNT              127 a    217 c    144 g    141 t
ORIGIN 42 bp upstream of HpaII site.

1 gatgttccag ggactgctgc tgtggctgct gctgggcgtg gccggggtgt gggcttccag 61 ggggccactg cggccgctgt gccagcccat caacgccacc ctggcggctg agaaggaggc 121 ctgccctgtc tgtatcactt tcaccaccag catctgcgcc ggctactgcc ccagcatgaa 181 gcgggtgctg cctgtcatcc tgccgcccat gccccagcgg gtgtgcacct accatgagct 241 gcgcttcgcc tccgttcggc tccccggctg cccacctgga gtggacccaa tggtctcctt 301 ccccgtggcc ctcagctgtc actgtggatc ctgccgcctc agcagcactg actgcggggg 361 tcccagaacc caacccttgg cctgtgacca cccccgctc ccagacatcc tcttcctcta 421 aggatgcccc acttcaacct cccatgccca tcctaactct ggaaaccagc agacactctt
```

```
481 cccctccctt cccaataaag acttctcaaa ctgcctaggc tggcctaata ataattgtaa 541 tcattattaa cccagaagtt cttcaaatat aagattaaaa agatgaacag atataattct 601 taccctattt aaagacaaaa gagttttct
```

SEQ. ID. NO:3
NM_173901. Bos taurus glycop...[gi:27806912]
LOCUS       NM_173901     731 bp    mRNA    linear    MAM 05-OCT-2003
DEFINITION  Bos taurus glycoprotein hormones, alpha polypeptide (CGA), mRNA.
ACCESSION   NM_173901
VERSION     NM_173901.1  GI:27806912
KEYWORDS    .
SOURCE      Bos taurus (cow)
  ORGANISM  Bos taurus
            Eukaryota; Metazoa; Chordata; Craniata; Vertebrata; Euteleostomi;
            Mammalia; Eutheria; Cetartiodactyla; Ruminantia; Pecora; Bovoidea;
            Bovidae; Bovinae; Bos.
REFERENCE   1  (bases 1 to 731)
  AUTHORS   Goodwin,R.G., Moncman,C.L., Rottman,F.M. and Nilson,J.H.
  TITLE     Characterization and nucleotide sequence of the gene for the common
            alpha subunit of the bovine pituitary glycoprotein hormones
  JOURNAL   Nucleic Acids Res. 11 (19), 6873-6882 (1983)
  MEDLINE   84041490
  PUBMED    6314263
REFERENCE   2  (bases 1 to 731)
  AUTHORS   Erwin,C.R., Croyle,M.L., Donelson,J.E. and Maurer,R.A.
  TITLE     Nucleotide sequence of cloned complementary deoxyribonucleic acid
            for the alpha subunit of bovine pituitary glycoprotein hormones
  JOURNAL   Biochemistry 22 (20), 4856-4860 (1983)
  MEDLINE   84024633
  PUBMED    6688736
COMMENT     PROVISIONAL REFSEQ: This record has not yet been subject to final
            NCBI review. The reference sequence was derived from X00003.1.
FEATURES             Location/Qualifiers
     source          1..731
                     /organism="Bos taurus"
                     /mol_type="mRNA"
                     /db_xref="taxon:9913"
                     /chromosome="9"
                     /map="9"
     gene            1..731
                     /gene="CGA"
                     /db_xref="GeneID:280749"
                     /db_xref="LocusID:280749"
     CDS             101..463
                     /gene="CGA"
                     /note="chorionic gonadotropin, alpha chain"
                     /codon_start=1
                     /product="glycoprotein hormones, alpha polypeptide"
                     /protein_id="NP_776326.1"
                     /db_xref="GI:27806913"
                     /db_xref="GeneID:280749"
                     /db_xref="LocusID:280749"

/translation="MDYYRKYAAVILAILSLFLQILHSFPDGEFTMQGCPECKLKENK

YFSKPDAPIYQCMGCCFSRAYPTPARSKKTMLVPKNITSEATCCVAKAFTKATVMGN

V

RVENHTECHCSTCYYHKS"

sig_peptide     101..172
                     /gene="CGA"
     misc_feature    173..460
                     /gene="CGA"
                     /note="hormone6; Region: Glycoprotein hormone"
                     /db_xref="CDD:pfam00236"
     mat_peptide     173..460
                     /gene="CGA"
                     /product="unnamed"
                     /label=pit_mat
     misc_feature    200..460
                     /gene="CGA"
                     /note="GHA; Region: Glycoprotein hormone alpha chain
                     homologues. Also called gonadotropins. Glycoprotein
                     hormones consist of two glycosylated chains (alpha and
                     beta) of similar topology"
                     /db_xref="CDD:smart00067"
ORIGIN -continued

```
  1 gcagttgctg agaaatcaca agacaaaact aaaattcttc ttcagatcca cagtcaactg
 61 ccctgactac attctgcaaa aatccagagg acgaagagcc atggattact acagaaaata
121 tgcagctgtc attctggcca ttttgtctct gtttctgcaa attctccatt cctttcctga
181 tggagagttt acaatgcagg gctgtcctga atgcaagcta aagaaaaca aatacttctc
241 caagccagat gctccaatct atcagtgcat ggggtgctgc ttctccaggg catacccac
301 tccagcgagg tctaagaaga caatgttggt ccccaagaac atcacctcgg aagctacatg
361 ctgtgtggcc aaagcattta ccaaggccac agtgatggga aatgtcagag tggagaacca
421 caccgagtgc cactgcagca cttgttatta tcacaaatcc taatagtttg cagtgggcct
481 tgctgatgat ggctgacttg ctcaaaagga aaattaattt gtccagtgtc tatggctttg
541 tgagataaaa ccctcctttt ccttgccata ccatttttaa cctgctttga gaatatactg
601 cagctttatt gcttttctcc ttatcctaca atataatcag tagtcttgat cttttcattt
661 ggaatgaaat atggcattta gcatgaccat aaaaagctga ttccactgga aataaagtct
721 tttaaatcat c
```

SEQ. ID. NO:4
NM_173930. Bos taurus lutein...[gi:27806854]
LOCUS       NM_173930               426 bp    mRNA    linear   MAM 05-OCT-2003
DEFINITION  Bos taurus luteinizing hormone beta polypeptide (LHB), mRNA.
ACCESSION   NM_173930
VERSION     NM_173930.1  GI:27806854
KEYWORDS
SOURCE      Bos taurus (cow)
  ORGANISM  Bos taurus
            Eukaryota; Metazoa; Chordata; Craniata; Vertebrata; Euteleostomi;
            Mammalia; Eutheria; Cetartiodactyla; Ruminantia; Pecora; Bovoidea;
            Bovidae; Bovinae; Bos.
REFERENCE   1  (bases 1 to 426)
  AUTHORS   Virgin,J.B., Silver,B.J., Thomason,A.R. and Nilson,J.H.
  TITLE     The gene for the beta subunit of bovine luteinizing hormone encodes
            a gonadotropin mRNA with an unusually short 5'-untranslated region
  JOURNAL   J. Biol. Chem. 260 (11), 7072-7077 (1985)
  MEDLINE   85207729
  PUBMED    2987241
REFERENCE   2  (bases 1 to 426)
  AUTHORS   Maurer,R.A.
  TITLE     Analysis of several bovine lutropin beta subunit cDNAs reveals
            heterogeneity in nucleotide sequence
  JOURNAL   J. Biol. Chem. 260 (8), 4684-4687 (1985)
  MEDLINE   85182575
  PUBMED    3838746
COMMENT     PROVISIONAL REFSEQ: This record has not yet been subject to final
            NCBI review. The reference sequence was derived from M11506.1.
FEATURES             Location/Qualifiers
     source          1..426
                     /organism="Bos taurus"
                     /mol_type="mRNA"
                     /db_xref="taxon:9913"
                     /chromosome="18"
                     /map="18"
     gene            1..426
                     /gene="LHB"
                     /db_xref="GeneID:280839"
                     /db_xref="LocusID:280839"
     CDS             1..426
                     /gene="LHB"
                     /note="precursor"
                     /codon_start=1
                     /product="luteinizing hormone beta polypeptide"
                     /protein_id="NP_776355.1"
                     /db_xref="GI:27806855"
                     /db_xref="GeneID:280839"
                     /db_xref="LocusID:280839"

/translation="MEMFQGLLLWLLLGVAGVWASRGPLRPLCQPINATLAAEKEACP

VCITFTTSICAGYCPSMKRVLPVILPPMPQRVCTYHELRFASVRLPGCPPGVDPMVSF

PVALSCHCGPCRLSSTDCGGPRTQPLACDHPPLPDILFL"

-continued

```
    sig_peptide     1..60
                    /gene="LHB"
    mat_peptide     61..423
                    /gene="LHB"
                    /product="luteinizing hormone beta polypeptide"
    misc_feature    73..393
                    /gene="LHB"
                    /note="GHB; Region: Glycoprotein hormone beta chain
                    homologues. Also called gonadotropins. Glycoprotein
                    hormones consist of two glycosylated chains (alpha and
                    beta) of similar topology"
                    /db_xref="CDD:smart00068"
    variation       68
                    /gene="LHB"
                    /note="g in DNA; a in cDNA"
                    /replace="a"
    variation       81..82
                    /gene="LHB"
                    /note="gc in DNA; cg in cDNA"
                    /replace="cg"
ORIGIN 1  atggagatgt tccagggact gctgctgtgg ctgctgctgg gcgtggccgg ggtgtgggct 61  tccaggggc cactgcggcc gctgtgccag cccatcaacg ccaccctggc ggctgagaag 121  gaggcctgcc ctgtctgtat cactttcacc accagcatct gcgccggcta ctgccccagc 181  atgaagcggg tgctgcctgt catcctgccg cccatgcccc agcgggtgtg cacctaccat 241  gagctgcgct tcgcctccgt tcggctcccc ggctgcccac tggagtggga cccaatggtc 301  tccttccccg tggccctcag ctgtcactgt ggaccctgcc gcctcagcag cactgactgc 361  gggggtccca gaacccaacc cttggcctgt gaccaccccc cgctcccaga catcctcttc 421  ctctaa
```

---

We claim:

1. A method for maintaining one or more pregnancies by inducing accessory corpus luteum formation in one or more mammals, wherein insemination has been performed on said mammals and said mammals are bovine, said method comprising administering from about 25 micrograms to about 1 milligram of single chain recombinant bovine luteinizing hormone to said mammals on about Day 4 to about Day 7 after insemination, wherein administration of said single chain recombinant bovine luteinizing hormone induces accessory corpus luteum formation.

2. The method of claim 1 wherein pregnancies are maintained in more than about 40% of said mammals.

3. The method of claim 1 wherein pregnancies are maintained in more than about 50% of said mammals.

4. The method of claim 1 wherein said effective amount is between about 25 micrograms and about 250 micrograms.

5. The method of claim 1 wherein said effective amount is between about 75 micrograms and about 175 micrograms.

6. The method of claim 1 comprising administering said luteinizing hormone on about Day 4 to about Day 5 after said insemination.

7. The method of claim 1 wherein said pregnancy is maintained at about Day 15 after said insemination.

8. The method of claim 1 wherein said pregnancy is maintained at about Day 30 after said insemination.

9. The method of claim 1 wherein said pregnancy is maintained at about Day 56 after said insemination.

10. The method of claim 1 wherein administration is intramuscular.

11. The method of claim 1, comprising administering from about 75 micrograms to about 1 milligram bovine luteinizing hormone to said one or more mammals on about Day 4 to about Day 5 after said insemination.

12. The method of claim 11 comprising administering from about 75 micrograms to about 175 micrograms bovine luteinizing hormone to said one or more mammals on about Day 4 to about Day 5 after said insemination.

* * * * *